US012661045B2

(12) United States Patent
Hyodo

(10) Patent No.: US 12,661,045 B2
(45) Date of Patent: Jun. 23, 2026

(54) SIGNAL PROCESSING APPARATUS AND METHOD

(71) Applicant: SONY GROUP CORPORATION, Tokyo (JP)

(72) Inventor: Yasuhide Hyodo, Tokyo (JP)

(73) Assignee: Sony Group Corporation, Tokyo (JP)

( * ) Notice: Subject to any disclaimer, the term of this patent is extended or adjusted under 35 U.S.C. 154(b) by 244 days.

(21) Appl. No.: 18/576,473

(22) PCT Filed: Feb. 22, 2022

(86) PCT No.: PCT/JP2022/007140
§ 371 (c)(1),
(2) Date: Jan. 4, 2024

(87) PCT Pub. No.: WO2023/286313
PCT Pub. Date: Jan. 19, 2023

(65) Prior Publication Data
US 2024/0306967 A1     Sep. 19, 2024

(30) Foreign Application Priority Data

Jul. 15, 2021     (JP) ................................. 2021-117097

(51) Int. Cl.
*A61B 5/16*          (2006.01)
*A61B 5/00*          (2006.01)
*A61B 5/02*          (2006.01)

(52) U.S. Cl.
CPC ................ *A61B 5/165* (2013.01); *A61B 5/02* (2013.01); *A61B 5/7221* (2013.01); *A61B 5/7264* (2013.01)

(58) Field of Classification Search
CPC ........... A61B 5/02; A61B 5/165; A61B 5/372; A61B 5/4266; A61B 5/6801;
(Continued)

(56) References Cited

U.S. PATENT DOCUMENTS 8,463,595 B1     6/2013  Rehling
2015/0173631 A1   6/2015  Richards
(Continued)

FOREIGN PATENT DOCUMENTS

CN     108042145 A     5/2018
JP     2009282686 A    12/2009
(Continued)

OTHER PUBLICATIONS

English Translation of International Search Report prepared by the Japan Patent Office on May 2, 2022, for International Application No. PCT/JP2022/007140, 2 pgs.
(Continued)

*Primary Examiner* — Michael T Rozanski
(74) *Attorney, Agent, or Firm* — SHERIDAN ROSS P.C.

(57) ABSTRACT

The present technology relates to a signal processing apparatus and a method that enable improvement in the robustness of emotion estimation against noise. A signal processing apparatus extracts, on the basis of a measured biological signal, a physiological measure contributing to an emotion as a feature amount, outputs, with respect to time-series data about the feature amount, time-series data about a prediction label of an emotion status by a discriminative model built in advance, and outputs an emotion estimation result on the basis of a result of performing weighted summation of the prediction label with prediction label reliability that is reliability of the prediction label. The present technology can be applied to an emotion estimation processing system.

15 Claims, 19 Drawing Sheets

(58) Field of Classification Search
CPC ... A61B 5/7203; A61B 5/7207; A61B 5/7221;
A61B 5/7264
See application file for complete search history.

(56) References Cited

U.S. PATENT DOCUMENTS

| | | | |
|---|---|---|---|
| 2017/0316164 A1 | 11/2017 | Casale | |
| 2021/0307621 A1 | 10/2021 | Svenson et al. | |

FOREIGN PATENT DOCUMENTS

| | | |
|---|---|---|
| JP | 2019-170967 | 10/2019 |
| JP | 2020-048622 | 4/2020 |
| JP | 2020068973 A | 5/2020 |
| JP | 2020-203051 | 12/2020 |
| JP | 2021-053261 | 4/2021 |
| KR | 20210047477 A | 4/2021 |
| WO | WO-2017136938 A1 | 8/2017 |
| WO | WO 2018/218286 | 12/2018 |
| WO | WO-2021200503 A1 | 10/2021 |

OTHER PUBLICATIONS

Val-Calvo et al., "Optimization of Real-Time EEG Artifact Removal and Emotion Estimation for Human-Robot Interaction Applications," Frontiers in Computational Neuroscience, vol. 13, No. 80, Nov. 26, 2019, 13 pages.

Calculate reliability of representative value
of prediction label as consecutive values [-1 to 1]
(Perform weighted summation of prediction labels of plurality of events)

$$r(t) = \sum_i w_i c_i y_i \Delta t_i \Big/ \sum_i w_i \Delta t_i \qquad \cdots (1)$$

Forgetting factor

Reliability of
prediction label
(0.0 to 1.0)

Prediction label (positive class:
1/negative class: -1)

Event continuation time

Discretize prediction labels [0 or 1]
(Perform threshold processing on r and calculate representative value z
of prediction label as emotion estimation result)

$$z(t) = \begin{cases} 0 \,(\text{if } r(t) < 0) \\ 1 \,(\text{if } r(t) > 0) \\ \text{previous value}\,(\text{otherwise}) \end{cases} \qquad \cdots (2)$$

FIG.10

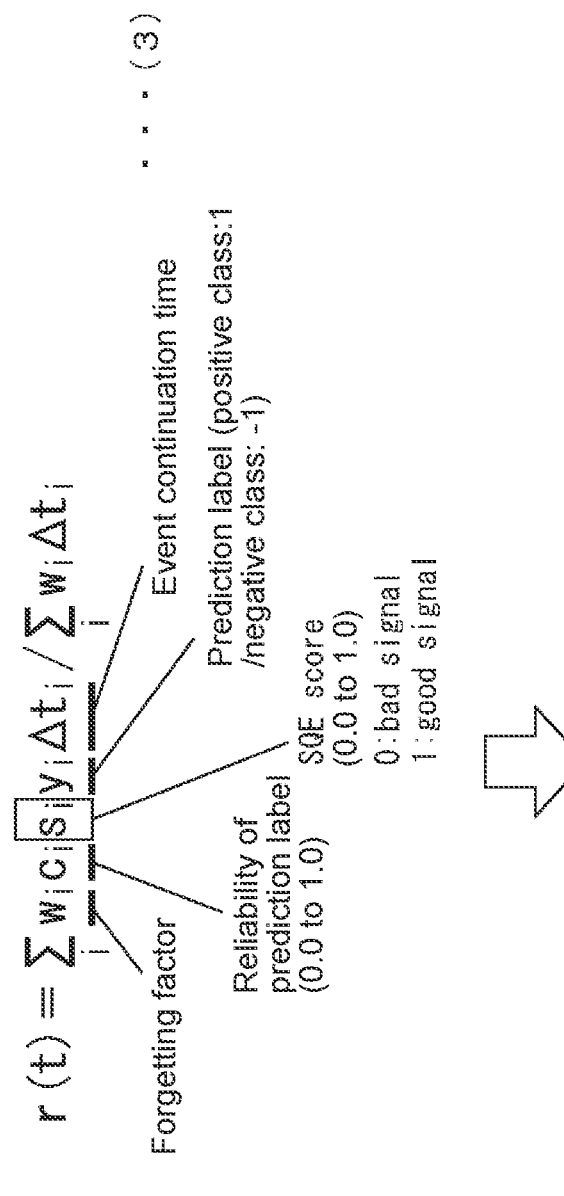

Calculate reliability of representative value of prediction label as consecutive values [-1 to 1] (Perform weighted summation of prediction labels of plurality of events)

$$r(t) = \sum_i w_i c_i |s_i| y_i \Delta t_i / \sum_i w_i \Delta t_i \quad \cdots (3)$$

Forgetting factor

Reliability of prediction label (0.0 to 1.0)

SQE score (0.0 to 1.0)
0: bad signal
1: good signal

Prediction label (positive class: 1 /negative class: -1)

Event continuation time

Discretize prediction labels [0 or 1] (Perform threshold processing on r and calculate representative value z of prediction label as emotion estimation result)

$$z(t) = \begin{cases} 0 \ (if \ r(t) < 0) \\ 1 \ (if \ r(t) > 0) \\ previous \ value \ (otherwise) \end{cases} \quad \cdots (2)$$

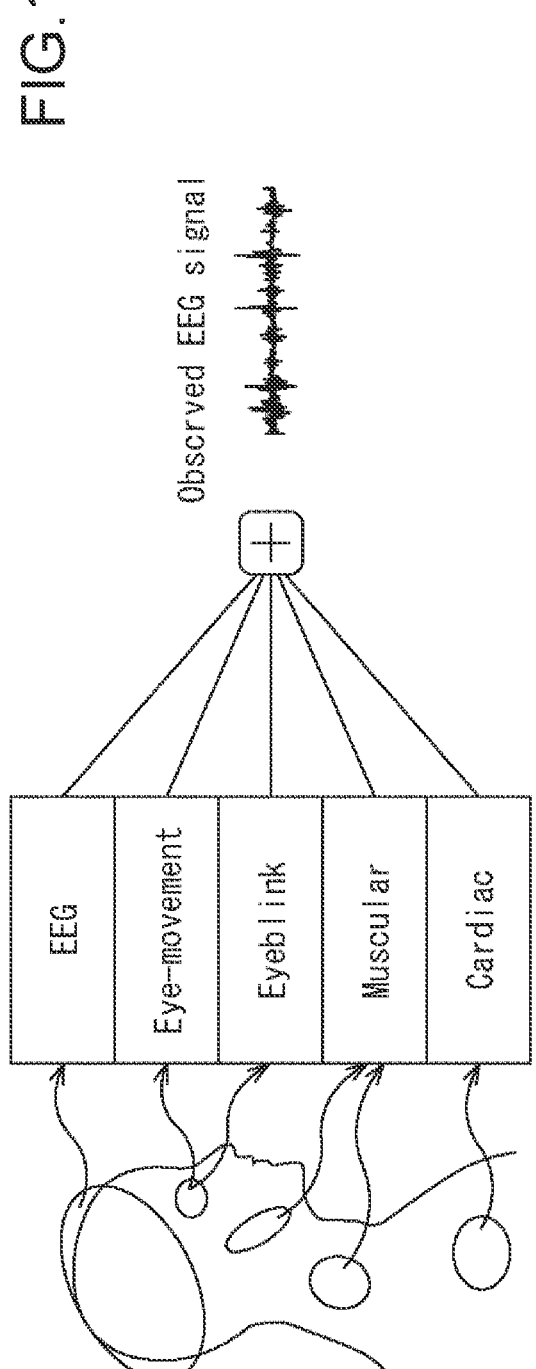

Observed EEG signal

EEG

Eye-movement

Eyeblink

Muscular

Cardiac $m$ : SQE discriminative class $\alpha_m$ : Class label corresponding on SQE discriminative class (previous setting [0, 1])

$c_m$ : Reliability of class label (that depends on input signal [0, 1])

$f()$ : Look-up table for adjustment (previous setting [0, 1])

$$s_m = \alpha_m f(d_m) \qquad \cdots (5)$$

- Examples of $\alpha_m, f(d_m)$ :
  - EEG clean → $\alpha_m$=1. 0 (that is not noise. $f(d_m)$ monotonically increases)
  - Eye-movement → $\alpha_m$=0. 9 ($f(d_m)$ monotonically decreases)
  - Muscular → $\alpha_m$=0. 2(that is principally difficult to be cancelled. $f(d_m)$ monotonically decreases)
  - Cardiac → $\alpha_m$=0. 5 ($f(d_m)$ monotonically decreases)

- $\alpha_m$ is adjustment term and no limitations are imposed
- $f(d_m)$ is characterized in that it monotonically increases in case where m is main signal and it monotonically decreases in case where m is noise

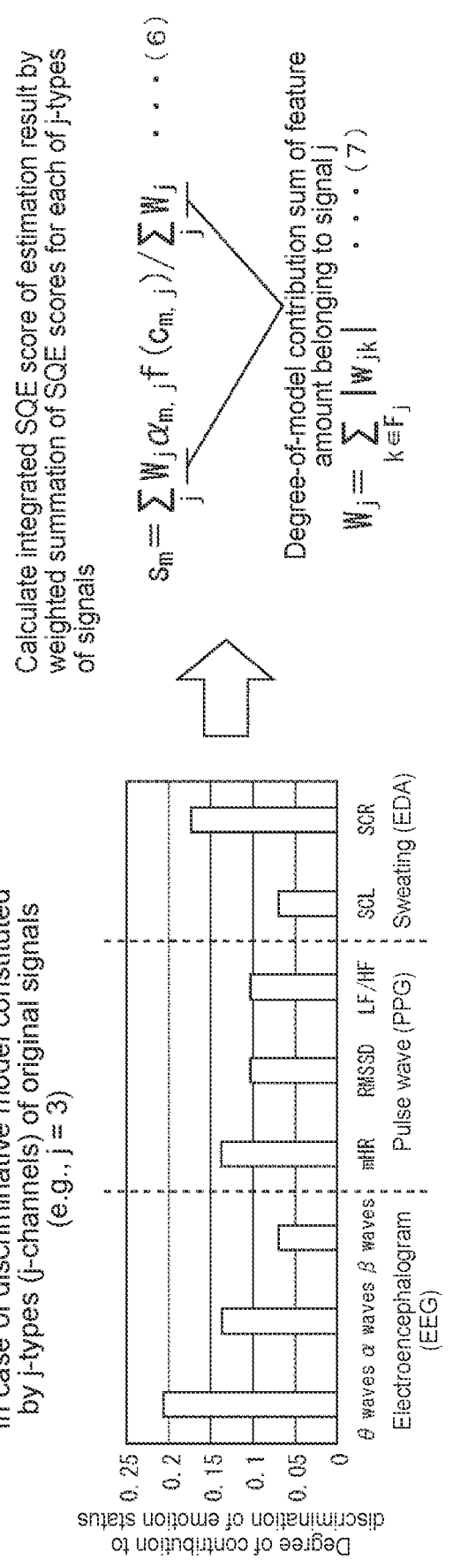

Calculate integrated SQE score of estimation result by weighted summation of SQE scores for each of j-types of signals $$S_m = \sum_j W_j \alpha_{m,j} f(c_{m,j}) / \sum_j W_j \quad \cdots (6)$$

Degree-of-model contribution sum of feature amount belonging to signal j $$W_j = \sum_{k \in F_j} |w_{jk}| \quad \cdots (7)$$

In case of discriminative model constituted by j-types (j-channels) of original signals (e.g., j = 3)

Degree of contribution to discrimination of emotion status 0.25
0.2
0.15
0.1
0.05
0

θ waves  α waves  β waves | mHR  RMSSD  LF/HF | SCL  SCR

Electroencephalogram (EEG) | Pulse wave (PPG) | Sweating (EDA)

FIG. 17

SIGNAL PROCESSING APPARATUS AND METHOD

CROSS REFERENCE TO RELATED APPLICATIONS

This application is a national stage application under 35 U.S.C. 371 and claims the benefit of PCT Application No. PCT/JP2022/007140, having an international filing date of 22 Feb. 2022, which designated the United States, which PCT application claimed the benefit of Japanese Patent Application No. 2021-117097, filed 15 Jul. 2021, the entire disclosures of each of which are incorporated herein by reference.

TECHNICAL FIELD

The present technology relates to a signal processing apparatus and a method and more particularly relates to a signal processing apparatus and a method that enable improvement in the robustness of emotion estimation against noise.

BACKGROUND ART

Physiological reactions such as electroencephalogram, heart rate, and sweating appear on a body surface when a human emotion changes. An emotion estimation system for estimating a human emotion reads these physiological reactions as biological signals through sensor devices. The emotion estimation system extracts feature amounts such as physiological measures contributing to the emotion by signal processing. The emotion estimation system estimates the user's emotion on the basis of the feature amounts by the use of a model determined by machine learning.

However, body movement noise is generated when the user moves in a case where such a technology is developed to an actual application. It lowers the signal quality, which leads to an error in an output result of emotion estimation.

In this context, Non-Patent Literature 1 has described an emotion estimation technology considering the noise influence. However, the technology according to Non-Patent Literature 1 has not provided an algorithm considering the reliability of noise cancellation and this technology has merely performed assessment combining noise cancellation with emotion estimation.

Moreover, an example of the conventional signal quality determination technology is a technology according to Patent Literature 1. The technology according to Patent Literature 1 determines a biological effective state in consideration of the reliability and finally outputs it. However, the determination approach for the biological effective state in Patent Literature 1 is limited to illuminance intensity and face orientations. It imposes a limitation on applications and situations where the technology can be applied.

CITATION LIST

Non-Patent Literature

Non-Patent Literature 1: Val-Calvo, Mikel, et al. "Optimization of real-time EEG artifact removal and emotion estimation for human-robot interaction applications." Frontiers in Computational Neuroscience 13(2019), Internet search <https://www.frontiersin.org/articles/10.3389/fn-com.2019.00080/ full searched on 15 Jun. 2021>

Patent Literature

Patent Literature 1: Japanese Patent Application Laid-open No. 2019-170967

DISCLOSURE OF INVENTION

Technical Problem

As described above, body movement noise is generated when the user moves in a case where the technology for estimating an emotion on the basis of biological signals is developed to an actual application. It lowers the signal quality, which leads to an error in an output result of emotion estimation.

The present technology has been made in view of such circumstances and enables improvement in the robustness of emotion estimation against noise.

Solution to Problem

A signal processing apparatus according to an aspect of the present technology includes:

a feature amount extraction unit that extracts, on the basis of a measured biological signal, a physiological measure contributing to an emotion as a feature amount;

an emotion status time-series labelling unit that outputs, with respect to time-series data about the feature amount, time-series data about a prediction label of an emotion status by a discriminative model built in advance; and a stabilization processing unit that outputs an emotion estimation result on the basis of a result of performing weighted summation of the prediction label with prediction label reliability that is reliability of the prediction label.

According to an aspect of the present technology, a physiological measure contributing to an emotion is extracted as a feature amount on the basis of a measured biological signal, and, with respect to time-series data about the feature amount, time-series data about a prediction label of an emotion status is output by a discriminative model built in advance. Then, an emotion estimation result is output on the basis of a result of performing weighted summation of the prediction label with prediction label reliability that is reliability of the prediction label.

BRIEF DESCRIPTION OF DRAWINGS

FIG. 10 A diagram showing a calculation method of calculating a representative value of a prediction label of the emotion status in the sliding window.

FIG. 14 A diagram showing a calculation method of calculating a representative value of a prediction label of the emotion status in the sliding window.

FIG. 16 A diagram showing an example of quality stability determination using an electroencephalogram.

FIG. 17 A diagram showing an example of calculating a weight of a signal quality score per each type and each channel.

MODE(S) FOR CARRYING OUT THE INVENTION

Figure 1:
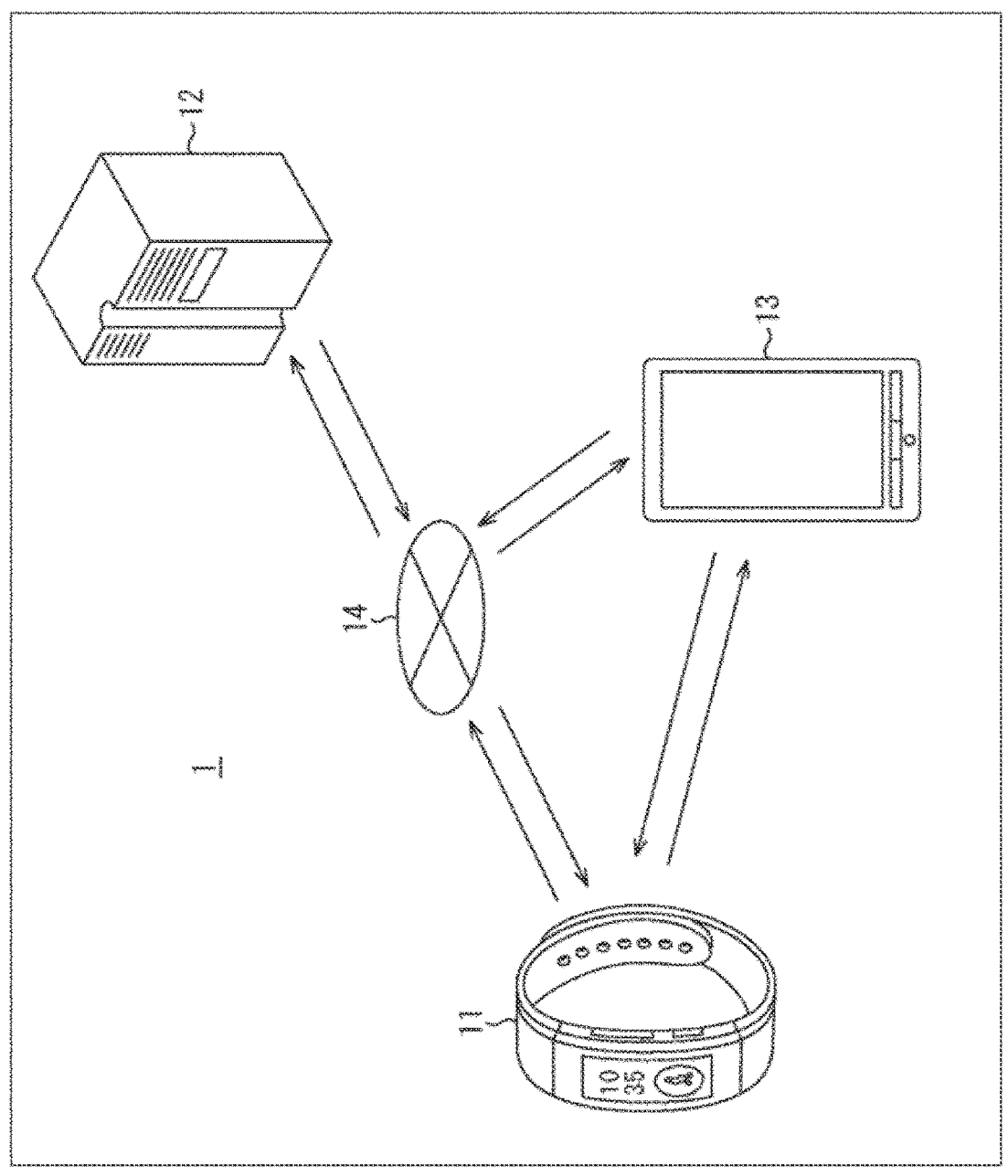
FIG. 1 A view showing a configuration example of an emotion estimation processing system according to an embodiment of the present technology.

Hereinafter, modes for carrying out the present technology will be described. The descriptions will be made in the following order.

1. Conventional Technology
2. System Configuration
3. First Embodiment
4. Second Embodiment
5. Others

1. Conventional Technology

Wearable devices for measuring human physiological reactions in daily life and sensing health and mental conditions have attracted more attention because of the booming of healthcare and wellness in the recent years.

When the human mind changes, the brain transmits signals through the autonomic nervous system, such that respective functions such as aspiration, skin temperature, sweating, and heart and blood vessel activities change. Central nervous activities such as an electroencephalogram that can be non-invasively measured on the human head and autonomic nervous system activities such as heart rate and sweating are known especially as physiological reactions indicating a human emotion (e.g., consciousness).

An electroencephalogram (EEG) can be measured by measuring activity potentials of the brain which actually leak out through the scalp, the skull, and the like typically by the use of electrodes attached to the scalp. It should be noted that a detection target area of a single electrode includes several million or more of nerve cells and this electrode detects the sum of activity potentials emitted from the numerous nerve cells.

It is known that signal frequency components such as θ waves, α waves, and β waves exhibit features as physiological measures of the electroencephalogram which contribute to the human emotion.

The heart rate can be measured by measurement of an electrical activity of the heart (electrocardiogram (ECG)) or by optical measurement (photoplethysmography (PPG)) of volumetric changes in blood when the heart pumps blood. The generally-known heart rate is one (average heart rate) calculated by taking an average of inverses of intervals between heartbeats. Moreover, the magnitude of variation between intervals between heartbeats is measured as a change in heart rate (heart rate variability) and various physiological measures indicating the variation are defined (LF, HF, LF/HF, percentage of adjacent normal-to-normal intervals (pNN) 50, root mean square successive difference (RMSSD), etc.).

The sweating (emotional sweating) appears on the body surface as a change (electrodermal activity (EDA)) in electrical conductance of the skin and can be electrically measured as a change in conductance value of the skin. It is called skin conductance. Physiological measures extracted from signals of the skin conductance are roughly classified into a skin conductance response (hereinafter, SCR) indicating an instantaneous sweating activity and a skin conductance level (hereinafter, SCL) indicating a gentle change in skin surface status. In this manner, the plurality of feature amounts indicating the autonomous nervous activity is defined.

An emotion estimation system for estimating an emotion of a user reads these physiological reactions as biological signals through sensor devices. The emotion estimation system extracts feature amounts such as physiological measures contributing to the emotion reaction by signal processing. The emotion estimation system estimates the user's emotion on the basis of the feature amounts by the use of a model determined by machine learning.

Such emotion estimation has been more deeply studied in the combination of the conventional physiological psychology and computing and the interdisciplinary fields along with the progress of machine learning technologies in recent years. Affective computing has been actively studied for example in the academic field of the emotion estimation mainly associated with engineering. Moreover, affective science has been actively studied in the academic field mainly associated with science.

It is desirable to achieve emotion estimation by sensing an autonomous nervous activity through a wearable device attachable to a wrist, an ear, etc. and easy to use in daily life in order to apply it to daily life and an actual environment. It is also desirable to achieve emotion estimation by sensing an electroencephalogram through a wearable device that can be naturally mounted on the head, e.g., a virtual reality (VR) head-mounted display or a wearable device naturally adaptable for the user's experience, e.g., an earphones- or headphones-type wearable device according to a technology for measuring an electroencephalogram inside/around an ear such as In-ear EEG/Around-ear EEG, which have been actively studied in recent years.

Moreover, it is desirable to achieve emotion estimation by multimodal analysis using both the electroencephalogram and the autonomous nervous activity in applications to realize them.

On the other hand, there is an influence of a user's body movement in applications in daily life and an actual environment. Since the biological signal typically has low signal intensity, it is necessary to improve the robustness against the noise influence due to the user's body movement in order to perform accurate sensing in daily life and an actual environment.

Technologies for reducing the noise influence due to the user's body movement are roughly classified into two approaches: (1) an approach of separating noise components by signal separation techniques such as adaptive filter, principal component analysis, and independent component analysis; and (2) an approach of analyzing a signal waveform and discriminating a class depending on the signal quality. These approaches have been studied and developed mainly in the fields of medical engineering and signal processing and also applied to products such as generally-used wearable heart rate sensors.

As described above, the productization and studies have been developed in order to improve the robustness against the noise influence due to the user's body movement. However, it is often principally difficult to completely cancel noise, and there are difficulties in achieving emotion estimation by use of the above-mentioned wearable devices.

A specific example of the conventional technologies can be the technology according to Non-Patent Literature 1. The technology according to Non-Patent Literature 1 introduces a noise reduction technology and assesses emotion estimation performance in order to improve the robustness against noise generated in an actual environment.

However, the technology according to Non-Patent Literature 1 merely introduces the noise cancellation technology during a pre-processing phase of emotion estimation. Therefore, the technology can robustly estimate the user's emotion when the noise cancellation sufficiently works, but the noise cancellation does not sufficiently work typically when modeling is statistically difficult. It can lower the emotion estimation accuracy.

The noise can be reduced by for example acquiring a noise reference signal and making use of statistic characteristics such as correlation analysis, principal component analysis, and independent component analysis. However, it is typically difficult to completely cancel the noise because the statistic processes are not constant in actual life.

An example of the relevant technologies can be the technology according to Patent Literature 1. The technology according to Patent Literature 1 determines a biological effective state in consideration of the reliability and finally outputs it. However, targets of the technology according to Patent Literature 1 are limited to the vehicle technologies and remote optical vital sensors and the determination approach for the biological effective state is limited to illuminance intensity and face orientations. It imposes a limitation on applications and situations where the technology can be applied.

In view of this, in the present technology, an emotion estimation result is output on the basis of a result of performing weighted summation of a prediction label with prediction label reliability that is reliability of the prediction label.

Accordingly, improvement in the robustness of emotion estimation against noise, improvement in the emotion estimation accuracy, and extension of the applications where the emotion estimation is applied can be expected.

Development to a variety of applications involving body movements specifically, for example, monitoring of a stress status in daily life, visualization of a concentrated status in an office environment, engagement analysis of a user while the user is watching video content, or excitement analysis during game play can be expected.

2. System Configuration

Configuration Example of Emotion Estimation System

FIG. 1 is a view showing a configuration example of an emotion estimation processing system according to an embodiment of the present technology.

The emotion estimation processing system 1 in FIG. 1 includes a biological information processing apparatus 11.

It should be noted that the emotion estimation processing system 1 may include a server 12, a terminal apparatus 13, and a network 14. In that case, in the emotion estimation processing system 1, the biological information processing apparatus 11, the server 12, and the terminal apparatus 13 are connected to one another via the network 14.

The emotion estimation processing system 1 is a system that detects a signal related to a status of a living body (hereinafter, referred to as biological signal) and estimates an emotion of the living body on the basis of the detected biological signal. For example, at least the biological information processing apparatus 11 of the emotion estimation processing system 1 is directly attached to the living body in order to detect the biological signal.

Figure 2:
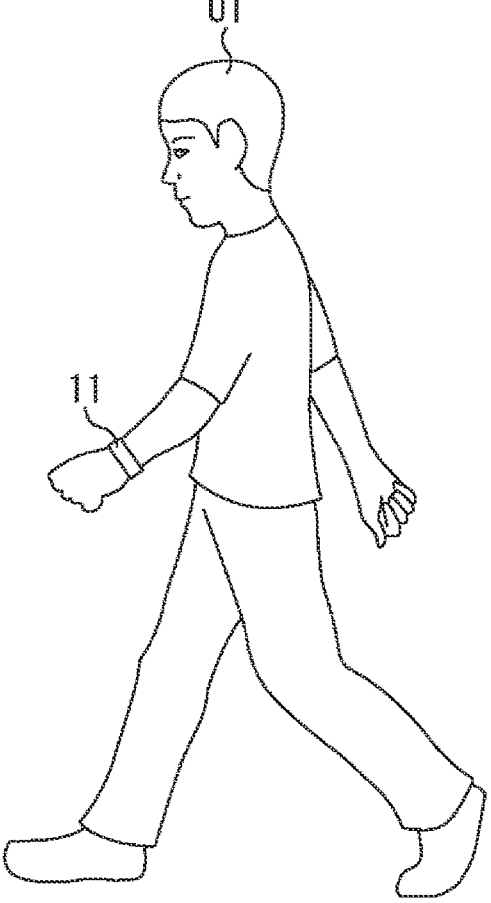
FIG. 2 A view showing a state in which a biological information processing apparatus is attached to a living body.
Figure 3:
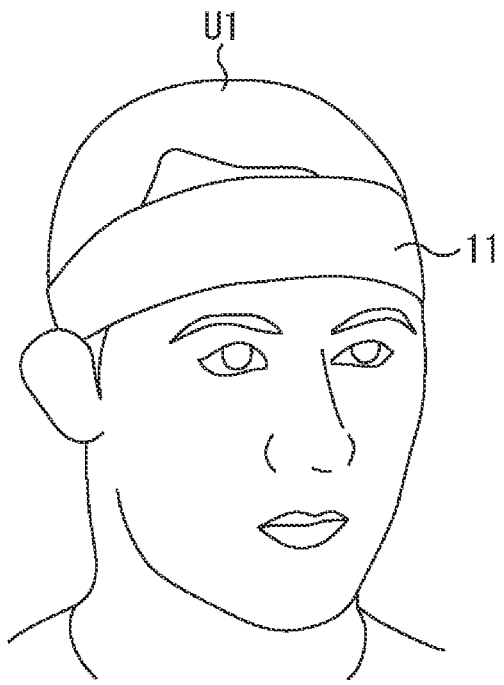
FIG. 3 A view showing a state in which the biological information processing apparatus is attached to the living body.

Specifically, the biological information processing apparatus 11 is used for estimating an emotion of the living body, for example, as shown in FIGS. 2 and 3.

FIGS. 2 and 3 are views showing a state in which the biological information processing apparatus 11 has been attached to the living body.

In the example in FIG. 2, the biological information processing apparatus 11 of a wristband-type such as a watch-type is attached to the wrist of a user U1.

In the example in FIG. 3, the biological information processing apparatus 11 of a headband-type such as a forehead contact-type is wrapped around the head of the user U1.

The biological information processing apparatus 11 includes a biological sensor. The biological sensor detects a biological signal for estimating an emotion of the living body, such as a sweating status, pulse waves, an electromyogram, a blood pressure, blood flow, and a body temperature of the user U1. The biological information processing apparatus 11 estimates an emotion of the user U1 on the basis of the biological signal detected by the biological sensor. A concentrated status, a conscious status, and the like of the user can be checked based on this emotion.

It should be noted that FIGS. 2 and 3 shows the examples in which the biological information processing apparatus 11 is attached to the arm or head. However, the attachment position of the biological information processing apparatus 11 is not limited to the examples in FIGS. 2 and 3.

For example, the biological information processing apparatus 11 may be realized in the form attachable to a portion of a hand, such as a wristband, gloves, a smartwatch, and a ring. Moreover, in a case where the biological information processing apparatus 11 is brought into contact with a portion of the living body, such as a hand, the biological information processing apparatus 11 may be in the form provided to an object that can be brought into contact with the user, for example. For example, the biological information processing apparatus 11 may be provided on a surface of an object that can be brought into contact with the user or the inside thereof. The object includes, for example, a portable terminal, a smartphone, a tablet, a mouse, a keyboard, a handle, a lever, a camera, a sports tool (e.g., a golf club, a tennis racquet, an archery bow), or stationery.

Figure 6:
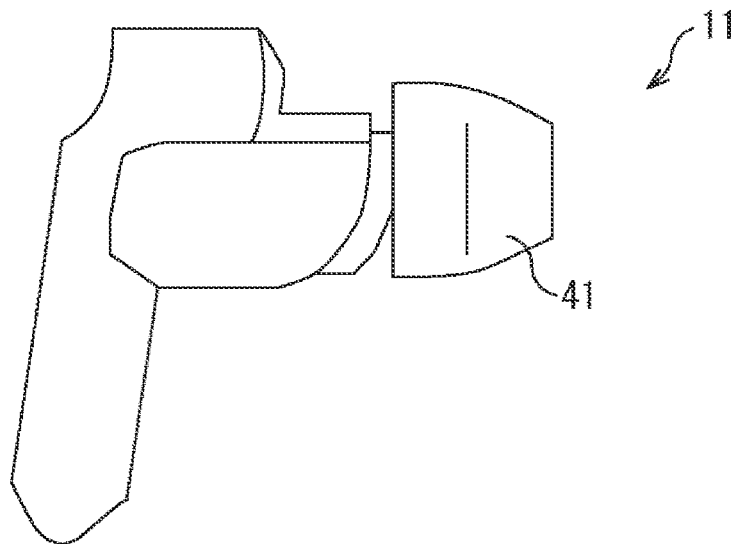
FIG. 6 A view showing another mode of the biological information processing apparatus.
Figure 7:
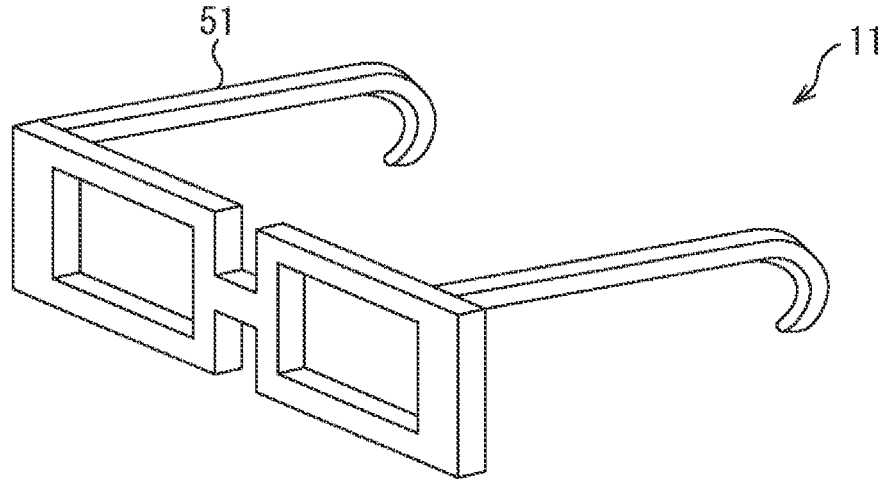
FIG. 7 A view showing another mode of the biological information processing apparatus.

Moreover, for example, the biological information processing apparatus 11 may be realized in the form attachable to a portion of the head or the ear of the user, such as a head-mounted display (FIG. 4), headphones (FIG. 5), earphones (FIG. 6), a hat, an accessory, goggles, or eyeglasses (FIG. 7).

FIGS. 4 to 7 are views showing other modes of the biological information processing apparatus 11.

Figure 4:
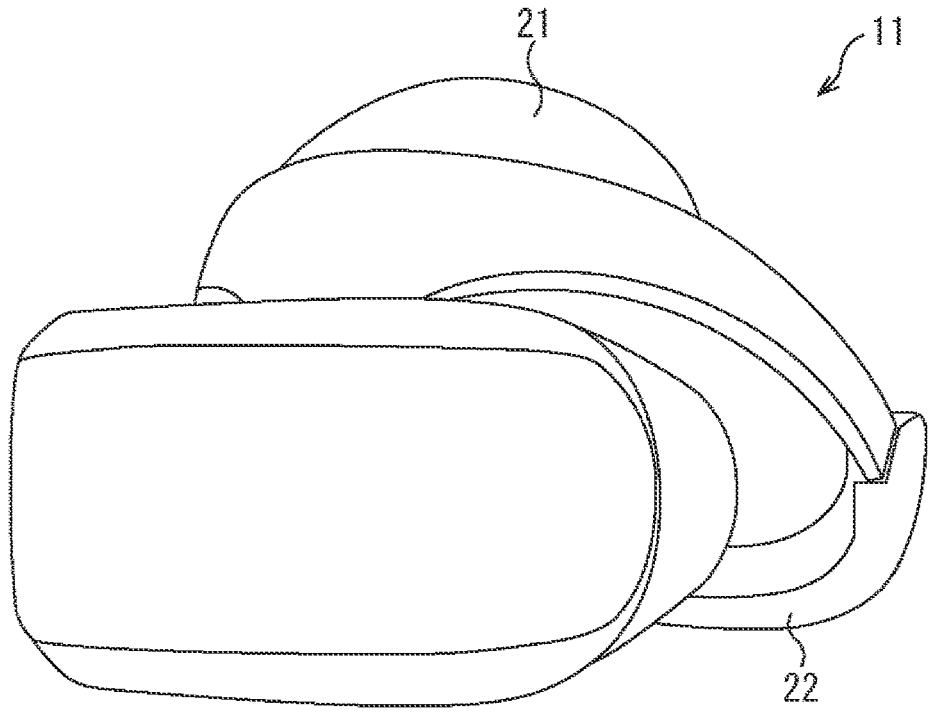
FIG. 4 A view showing another mode of the biological information processing apparatus.

FIG. 4 shows the biological information processing apparatus 11 of a head-mounted display-type.

In the biological information processing apparatus 11 of the head-mounted display-type, a pad portion 21 and a band portion 22 for example are attached to the user's head.

Figure 5:
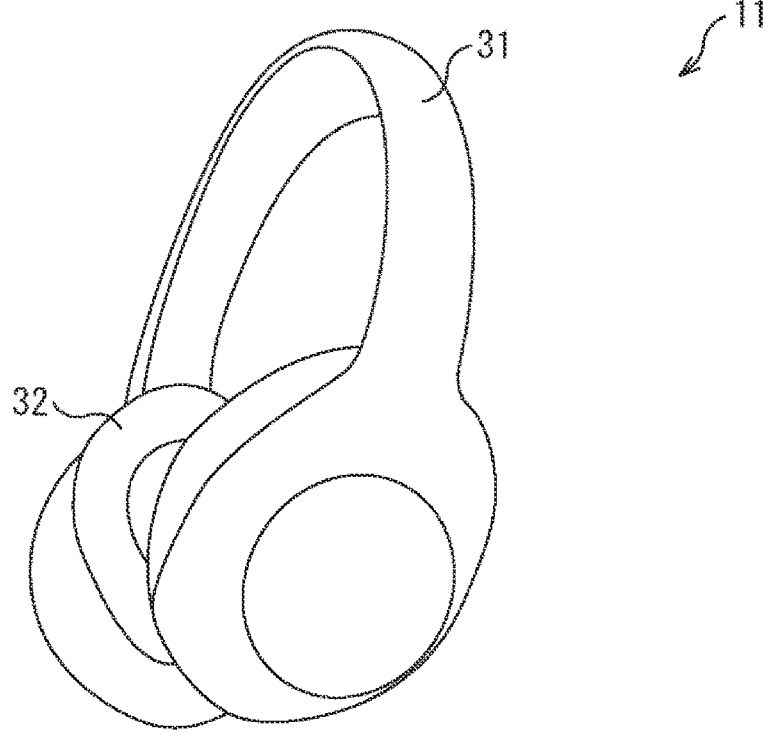
FIG. 5 A view showing another mode of the biological information processing apparatus.

FIG. 5 shows the biological information processing apparatus 11 of a headphones-type.

In the biological information processing apparatus 11 of the headphones-type, a band portion 31 and an ear pad 32 for example are attached to the user's head or ear.

FIG. 6 shows the biological information processing apparatus 11 of an earphones-type.

In the biological information processing apparatus 11 of the earphones-type, an earpiece 41 is attached to the user's ear.

FIG. 7 shows the biological information processing apparatus 11 of an eyeglasses-type.

In the biological information processing apparatus 11 of the eyeglasses-type, a temple 51 is attached to an upper portion of the user's ear.

Moreover, the biological information processing apparatus 11 may be provided to clothes such as a sportswear, socks, an underwear, a protector, shoes, or the like.

It should be noted that the attachment position and the attachment method of the biological information processing apparatus 11 are not particularly limited as long as the biological information processing apparatus 11 can detect signals related to the status of the living body. For example, the biological information processing apparatus 11 does not need to be brought into direct contact with the body surface of the living body. For example, the biological information processing apparatus 11 may be held in contact with the surface of the living body via for example clothes or a detection sensor protection film.

Moreover, in the emotion estimation processing system 1, the biological information processing apparatus 11 does not necessarily need to perform the processing alone. For example, the biological information processing apparatus 11 may include a biological sensor that is brought into contact with the living body, the biological sensor may send a detected biological signal to another device such as the server 12 and the terminal apparatus 13, and the other device may perform information processing on the basis of the received biological signal so as to estimate an emotion of the living body.

For example, in a case where the biological sensor has been attached to the user's arm or head for example, the biological information processing apparatus 11 may send a biological signal acquired from the biological sensor to the server 12 or the terminal apparatus 13 constituted by a smartphone for example and the server 12 or the terminal apparatus 13 may perform information processing so as to estimate an emotion of the living body.

The biological sensor provided in the biological information processing apparatus 11 detects a biological signal, held in contact with the surface of the living body in a wide variety of forms as described above. Therefore, changes in pressure of contact of the biological sensor with the living body due to the body movement of the living body easily influence a measurement result of the biological sensor. For example, the biological signal acquired from the biological sensor contains noise due to the body movement of the living body. It is desirable to accurately estimate an emotion of the living body on the basis of the biological signal containing such noise.

The body movement of the living body refers to general movement modes when the living body makes a movement. For example, the body movement of the living body can be a living body movement such as twisting the wrist and bending/extending the finger(s) when the user U1 wears the biological information processing apparatus 11 at the wrist. Those user's movements can cause changes in pressure of contact of the biological sensor included in the biological information processing apparatus 11 with the user U1.

It should be noted that the biological information processing apparatus 11 may include a second sensor and a third sensor to be described next other than the above-mentioned biological sensor in order to improve the accuracy of the biological signal obtained by the biological sensor.

For example, the second sensor is configured to detect changes in body movement of the living body. The third sensor is configured to detect changes in pressure of the living body in a detection area of the biological sensor.

In this case, in the biological information processing apparatus 11, the body movement noise in the biological signal detected by the biological sensor can be accurately reduced by using the body movement signal and the pressure signal respectively detected by the second sensor and the third sensor. In the biological information processing apparatus 11, emotion estimation processing according to the present technology to be described below may be performed by using the thus corrected biological signal.

Referring back to FIG. 1, the server 12 in the emotion estimation processing system 1 is constituted by a computer for example. The terminal apparatus 13 is constituted by a smartphone, a portable terminal, or a personal computer for example.

The server 12 and the terminal apparatus 13 receive information and signals sent from the biological information processing apparatus 11 via the network 14 and send the information and signals to the biological information processing apparatus 11.

The server 12 and the terminal apparatus 13 receive, for example, as described above, a biological signal obtained by the biological sensor included in the biological information processing apparatus 11 from the biological information processing apparatus 11 and perform signal processing on the received biological signal, thereby estimating an emotion of the living body.

The network 14 is constituted by the Internet or a wireless local area network (LAN) for example.

3. First Embodiment (Basic Configuration)

First Configuration Example of Biological Information Processing Apparatus

Figure 8:
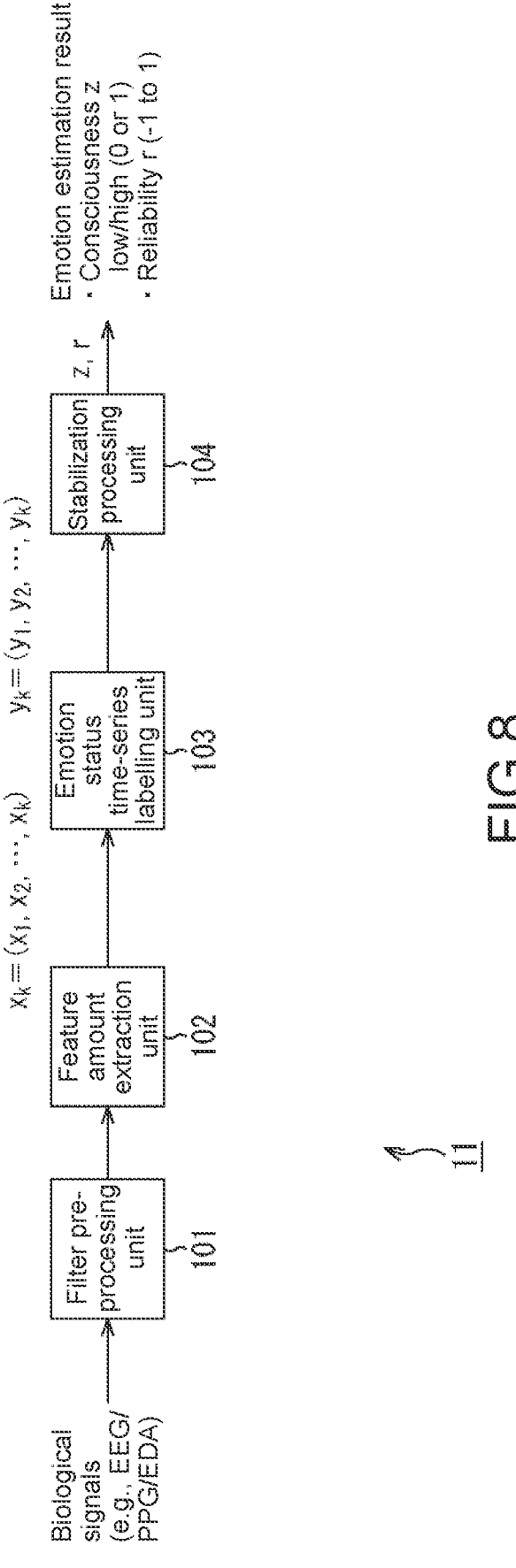
FIG. 8 A block diagram showing a first configuration example of the biological information processing apparatus.

FIG. 8 is a block diagram showing a first configuration example of the biological information processing apparatus 11.

In FIG. 8, the biological information processing apparatus 11 is constituted by a filter pre-processing unit 101, a feature amount extraction unit 102, an emotion status time-series labelling unit 103, and a stabilization processing unit 104.

The filter pre-processing unit 101 performs pre-processing such as band-pass filter and noise cancellation on the measured biological signal. The filter pre-processing unit 101 outputs the biological signal subjected to the pre-processing to the feature amount extraction unit 102.

For example, in a case where the biological signal is an electroencephalogram (EEG), the electroencephalogram is measured on the basis of activity potentials of the brain which leak out through the scalp, the skull, and the like after electrodes are attached to the scalp. It is known that the SN ratio is very low as one of features of the thus measured electroencephalogram. It is thus necessary to remove signals having unnecessary frequency components from the EEG that is time-series signals. The band-pass filter is applied (e.g., with a passband of 0.1 Hz to 40 Hz).

Moreover, body movement components due to the human body movement are superimposed on the biological signal as artifacts (e.g., noise other than target signals). In this regard, a signal processing technology such as adaptive filter and independent component analysis is applied. The filter pre-processing is performed also in a case where the biological signal is the emotional sweating (EDA), the pulse waves (PPG), the blood flow (LDF), or the like.

The feature amount extraction unit 102 extracts feature amount vectors $x=(x_1, x_2, \ldots, x_n)$ as model input variables for estimating an emotion status by using the biological signal supplied from the filter pre-processing unit 101. The feature amount extraction unit 102 outputs the extracted feature amount vectors $x=(x_1, x_2, \ldots, x_n)$ to the emotion status time-series labelling unit 103.

Specifically, the feature amount extraction unit 102 observes signals from a vital sensor (biological sensor), such as the electroencephalogram (EEG), the emotional sweating (EDA), the pulse waves (PPG), and the blood flow (LDF), as time-series data and extracts physiological measures contributing to changes in emotion as feature amounts. Here, although a method of extracting each feature amount is not limited, an example of the feature amount extraction will be described below.

For example, the electroencephalogram (EEG) can be measured by measuring activity potentials of the brain which leak out through the scalp, the skull, and the like by the use of the electrodes typically attached to the scalp as described above. Aftanas, L. I., and S. A. Golocheikine. "Human anterior and frontal midline theta and lower alpha reflect emotionally positive state and internalized attention: high-resolution EEG investigation of meditation." Neuroscience letters 310.1 (2001): 57-60 (hereinafter, referred to as Cited Document 1) has described that features of signal frequency components such as $\theta$ waves, $\alpha$ waves, and $\beta$ waves are extracted as physiological measures of the electroencephalogram which contribute to the human emotion.

On the other hand, the emotional sweating (EDA) is observed as time-series signals of the skin conductance (hereinafter, referred to as skin conductance signals) as described above. Benedek, M. & Kaernbach, C. (2010). A continuous measure of phasic electrodermal activity. Journal of Neuroscience Methods, 190, 80-91. (hereinafter, referred to as Cited Document 2) has described that the physiological measures extracted from the skin conductance signals are separated into a skin conductance response (SCR) indicating an instantaneous sweating activity and a skin conductance level (SCL) indicating a gentle change in skin surface status.

Moreover, the heart rate and changes in heart rate can be extracted from the pulse waves (PPG). The change in the heart rate can be physiological measures such as mHR, LF, HF, LF/HF, pNN50, and RMSSD.

In general, the feature amount is extracted by an analysis window (sliding window) for about five minutes. For example, Salahuddin, Lizawati, et al. "Ultra short term analysis of heart rate variability for monitoring mental stress in mobile settings." 2007 29th annual international conference of the ieee engineering in medicine and biology society. IEEE, 2007. (hereinafter, Cited Document 3) has described heart rate variability (HRV) of a short window of about several tens of seconds as ultra-short-term HRV further in consideration of real-timeness.

It should be noted that the feature amount is not limited to the physiologically-known feature amounts. The feature amount extraction unit 102 may perform signal processing of extracting feature amounts contributing to the emotion in a data-driven manner by, for example, deep learning or an autoencoder.

The emotion status time-series labelling unit 103 sets time-series feature amounts $X_k=(x_1, x_2, \ldots, x_k)$ in the sliding window out of the feature amount vectors x supplied from the feature amount extraction unit 102, as an input. The emotion status time-series labelling unit 103 discriminates prediction labels of the emotion status in a time-series by the use of a discriminative model that is a machine learning model built in advance and labels them as $Y_k=(y_1, y_2, \ldots, y_k)$.

The emotion status time-series labelling unit 103 outputs the time-series data $Y_k=(y_1, y_2, \ldots, y_k)$ of the prediction labels as a time-series labelling result of the emotion status to the stabilization processing unit 104. At this time, the emotion status time-series labelling unit 103 also outputs the reliability of the prediction label, which is obtained from the discriminative model.

An approach for the time-series labelling of the emotion status can be a discriminative model generally used in time-series data analysis or natural language processing. Specifically, examples of the approach can include support vector machine (SVM), k-nearest neighbor (k-NN), linear discriminant analysis (LDA), hidden markov models (HMM), conditional random fields (CRF), structured output support vector machine (SOSVM), Bayesian network, recurrent neural network (RNN), and long short term memory (LSTM). It should be noted that the approach is not limited.

The stabilization processing unit 104 performs weighted summation of the prediction labels of the emotion status in a time-series with the reliability of the prediction label of the emotion status in the sliding window by the use of the time-series data $Y_t=(y_1, y_2, \ldots, y_t)$ about the prediction label of the emotion status supplied from the emotion status time-series labelling unit 103. The stabilization processing unit 104 outputs a representative value (e.g., consciousness to be described later) z of the prediction label and reliability r of the representative value of the prediction label as an emotion estimation result. The reliability r of the representative value of the prediction label is reliability in calculating the representative value of the prediction label.

Specifically, the stabilization processing unit 104 performs weighted summation of the prediction label of the emotion status in the sliding window with the reliability of the prediction label, thereby calculating the reliability r of the representative value of the prediction label in the sliding window. In addition, the stabilization processing unit 104 performs threshold processing on the reliability r of the representative value of the prediction label and outputs a representative value z of the prediction label as an emotion estimation result.

Figure 9:
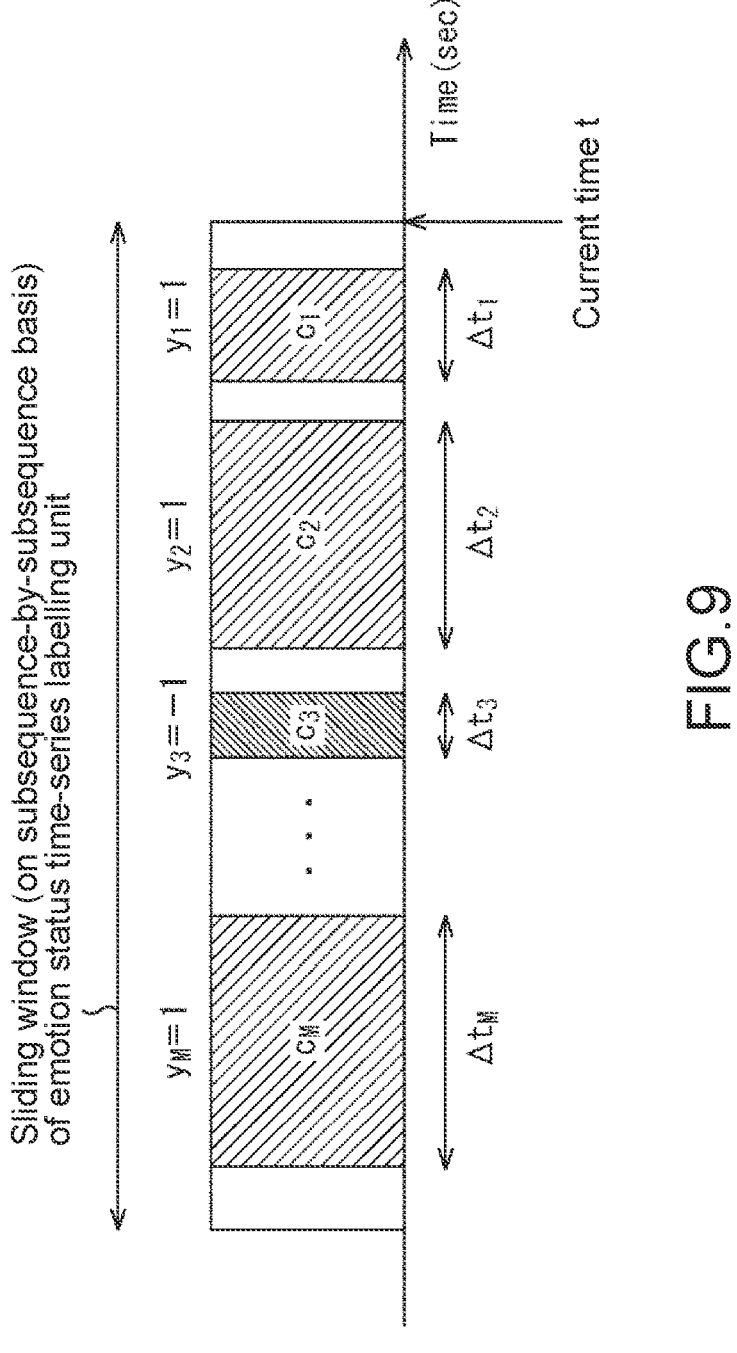
FIG. 9 A diagram showing an image in which time-series labelling of an emotion status is performed in a sliding window.

FIG. 9 is a diagram showing an image in which the stabilization processing unit 104 performs time-series labelling of the emotion status in the sliding window.

FIG. 9 shows the inside of the sliding window on a subsequence-by-subsequence basis.

In the figure, y denotes the prediction label of the emotion status, c denotes the reliability of the prediction label obtained from the discriminative model, and $\Delta t_i$ denotes the continuation time of the i-th event.

As shown in FIG. 9, y that is each prediction label of the emotion status is, for each event, calculated together with reliability c of the prediction label in the sliding window.

It should be noted that in a case where the prediction label y of the emotion status is discriminated on the basis of the consciousness, for example, the consciousness low/high is defined as one of two classes of 0 and 1.

Moreover, FIG. 9 shows an example in which the event continuation times are spaced apart from each other for the sake of description. However, the event continuation times do not need to be spaced apart from each other.

FIG. 10 is a diagram showing a calculation method of calculating, in the stabilization processing unit 104, the representative value of the prediction label in accordance with the prediction labels of the emotion status in a time-series in the sliding window and the reliability.

The reliability r of the representative value of the prediction label is calculated in accordance with the following expression (1).

[Expression 1]

$$r(t) = \sum_i w_i c_i y_i \Delta t_i / \sum_i w_i \Delta t_i \qquad (1)$$

Where i denotes an event number of one of a plurality of events detected in the sliding window, where y denotes the prediction label of the emotion status, c denotes the reliability of the prediction label obtained from the discriminative model, and $\Delta t_i$ denotes the continuation time of the i-th event. Moreover, w denotes a forgetting weight. This weight becomes smaller as it becomes older.

In accordance with Expression (1) above, with respect to the reliability of the prediction label of the emotion status in the plurality of events detected in the sliding window, reliability of the representative value of the prediction label in the sliding window is calculated as consecutive values of [−1 1].

In addition, a representative value z of the prediction label is calculated as an emotion estimation result by threshold-processing an output r of mathematical Expression (1) and substituting it into Expression (2) shown below.

[Expression 2]

$$z(t) = \begin{cases} 0 \ (\mathit{ifr}(t) < 0) \\ 1 \ (\mathit{ifr}(t) > 0) \\ \text{previous value (otherwise)} \end{cases} \qquad (2)$$

In Expression (2), the numeric value of the representative value z of the prediction label as the emotion estimation result depends on a definition of the prediction label y of the emotion status of the user.

For example, in a case where the prediction label of the emotion status is discriminated on the basis of the consciousness, the prediction label of the emotion status is defined as one of the two classes of 0 and 1, as the consciousness low/high. In this case, when the representative value z of the prediction label as the emotion estimation result is 0, the user's emotion status at the time of interest is discriminated as low consciousness (relax status). Moreover, when the representative value z of the prediction label as the emotion estimation result is 1, the user's emotion status at the time of interest is discriminated as high consciousness (conscious and concentrated status).

Processing of Apparatus

Figure 11:
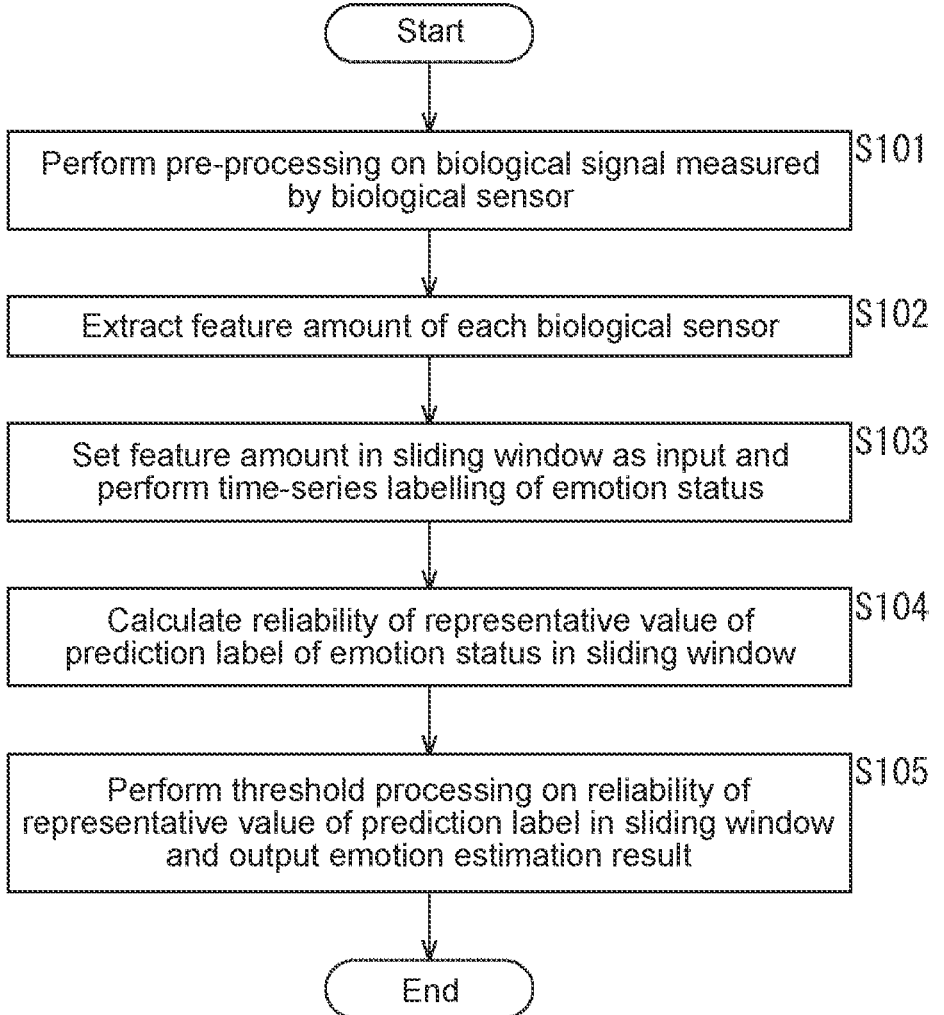
FIG. 11 A flowchart describing processing of the biological information processing apparatus in FIG. 8.

FIG. 11 is a flowchart describing processing of the biological information processing apparatus 11 in FIG. 8.

In Step S101, the filter pre-processing unit 101 performs pre-processing on a biological signal measured by the biological sensor. The filter pre-processing unit 101 outputs the biological signal subjected to the pre-processing to the feature amount extraction unit 102.

In Step S102, the feature amount extraction unit 102 extracts a feature amount on the basis of the biological signal supplied from the filter pre-processing unit 101. The feature amount extraction unit 102 outputs the extracted feature amount vectors $x=(x_1, x_2, \ldots, x_n)$ to the emotion status time-series labelling unit 103.

In Step S103, the emotion status time-series labelling unit 103 sets the feature amount in the sliding window out of the feature amounts supplied from the feature amount extraction unit 102, as an input, and performs time-series labelling of the emotion status. The emotion status time-series labelling unit 103 outputs the prediction labels of the emotion status in a time-series as a time-series labelling result of the emotion status to the stabilization processing unit 104.

In Step S104, the stabilization processing unit 104 sets the prediction labels of the emotion status in a time-series supplied from the emotion status time-series labelling unit 103, as an input, and calculates reliability r of the representative value of the prediction label in the sliding window in accordance with Expression (1) above.

In Step S105, the stabilization processing unit 104 performs threshold processing on the reliability r of the representative value of the prediction label in accordance with Expression (2) above and outputs the representative value z of the prediction label as the emotion estimation result.

As described above, in the first embodiment of the present technology, the emotion estimation result is output on the basis of a result of performing weighted summation of the prediction label with the prediction label reliability as the reliability of the prediction label. Accordingly, the robustness of the estimation accuracy of the emotion estimation is improved.

4. Second Embodiment (Additional Configuration)

Second Configuration of Apparatus

Figure 12:
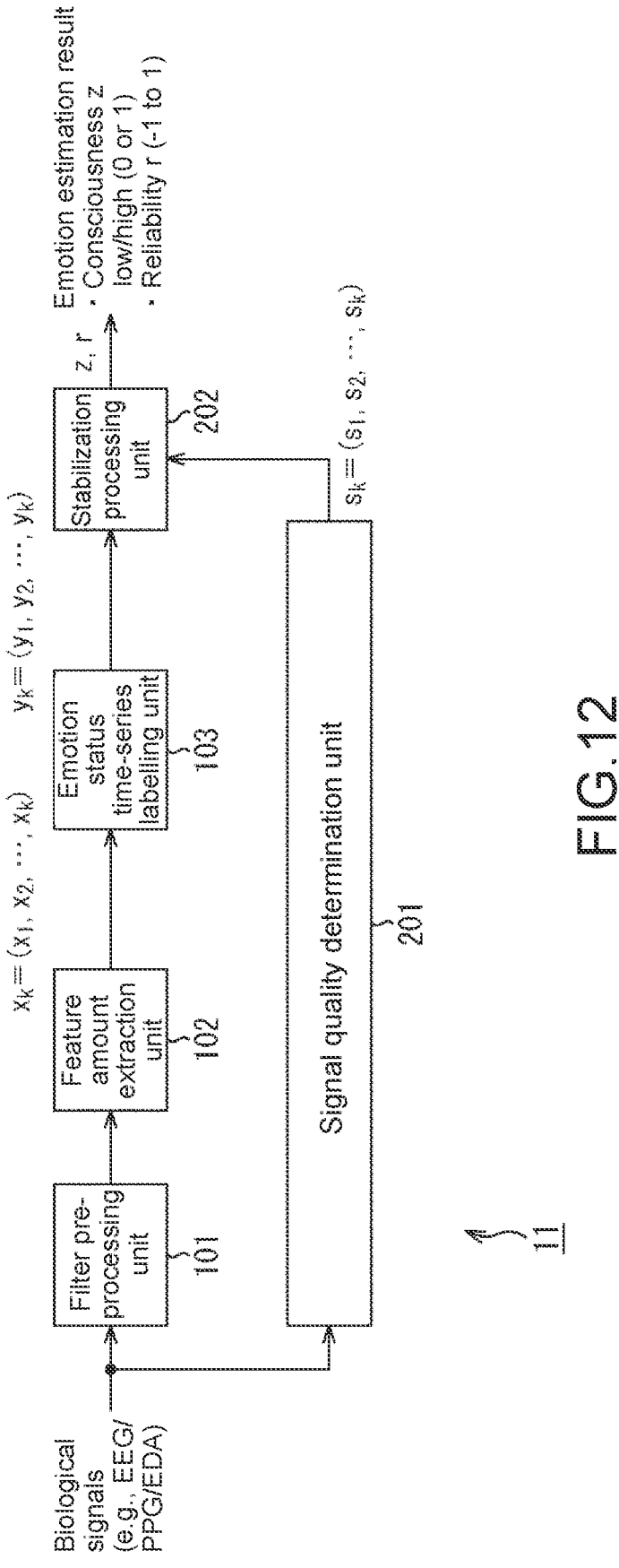
FIG. 12 A block diagram showing a second configuration example of the biological information processing apparatus.

FIG. 12 is a block diagram showing a second configuration example of the biological information processing apparatus 11.

In the second embodiment, a signal quality determination unit 201 is added in order to further improve the robustness of the emotion estimation against the noise in a case where a body movement for example causes noise in an actual environment.

That is, the biological information processing apparatus 11 in FIG. 12 is different from the biological information processing apparatus 11 in FIG. 8 in that the signal quality determination unit 201 is added and that a stabilization processing unit 202 replaces the stabilization processing unit 104. In FIG. 12, the portions corresponding to those of FIG. 8 are denoted by the same reference signs.

The signal quality determination unit 201 analyzes the waveform of the biological signal measured by the biological sensor and discriminates an artifact type. The signal quality determination unit 201 determines signal quality on the basis of the discrimination result and calculates a signal quality score as a signal quality determination result.

The stabilization processing unit 202 performs weighted summation with reliability of the prediction label of the emotion status and the signal quality score that is the determination result of the signal quality determination unit 201. The stabilization processing unit 202 outputs a representative value z of the prediction label and reliability r of the representative value of the prediction label as an emotion estimation result.

Figure 13:
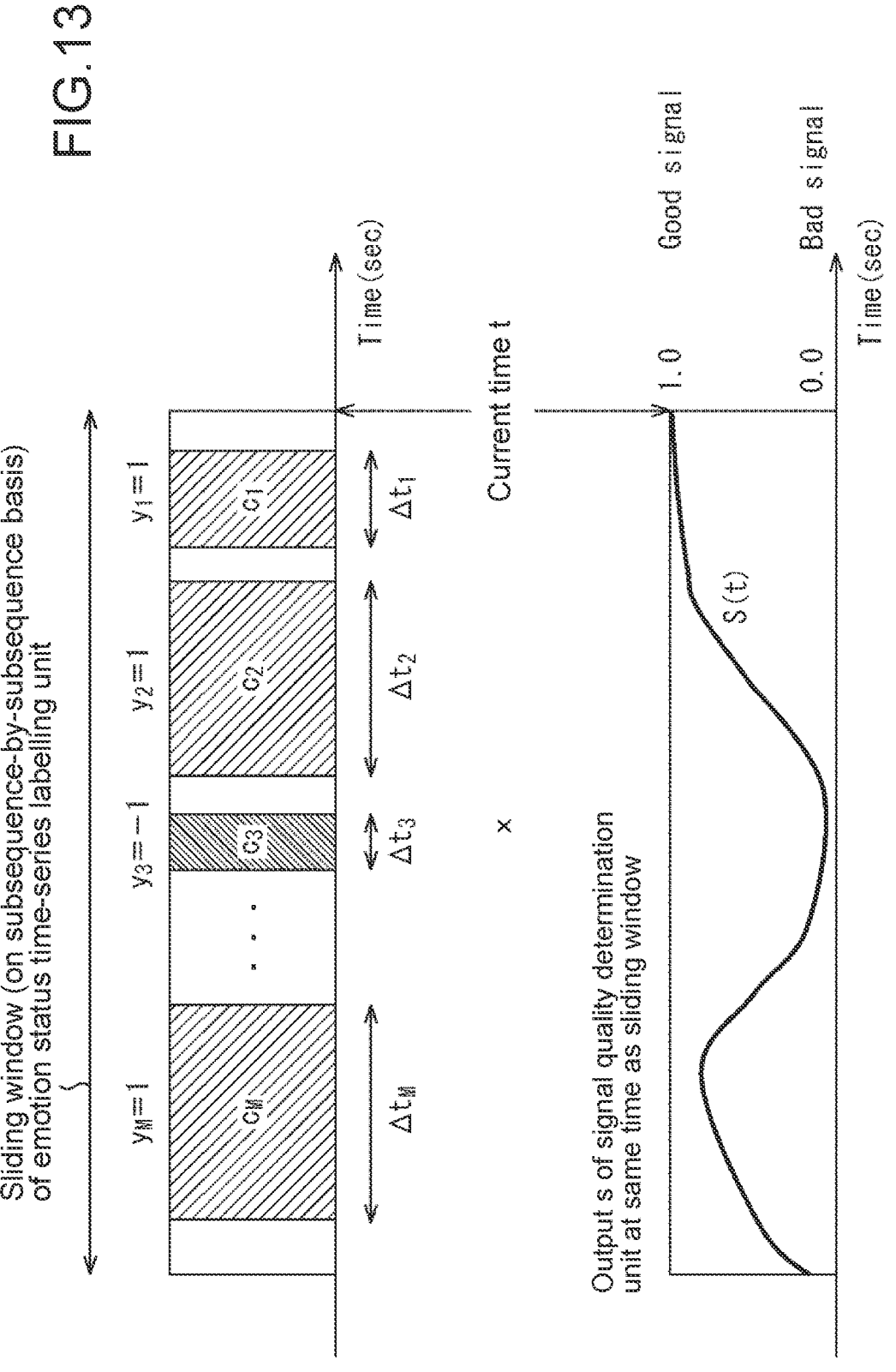
FIG. 13 A diagram showing an image in which time-series labelling of an emotion status is performed in a sliding window.

FIG. 13 is a diagram showing an image in which the stabilization processing unit 202 performs time-series labelling of the emotion status in the sliding window.

FIG. 13 shows the inside of the sliding window on a subsequence-by-subsequence basis as in FIG. 9. In the figure, y denotes the prediction label of the emotion status, c denotes the reliability of the prediction label obtained from the discriminative model, and $\Delta t_i$ denotes the continuation time of the i-th event.

In addition, FIG. 13 shows a signal quality score s that is the output of the signal quality determination unit 201 at the same time as the sliding window.

That is, in the stabilization processing unit 202 in FIG. 13, as in FIG. 9, y that is each prediction label of the emotion status is, for each event, calculated together with reliability c of the prediction label in the sliding window. In addition, the signal quality determination unit 201 outputs the signal quality score s to the stabilization processing unit 202 at the same time as the sliding window.

FIG. 14 is a diagram showing a calculation method of calculating, in the stabilization processing unit 202, the representative value of the prediction label in accordance with the prediction labels of the emotion status in the sliding window, the reliability, and the signal quality score.

The signal quality determination unit 201 calculates time-series data of the signal quality score s and outputs it to the stabilization processing unit 202. The stabilization processing unit 202 uses this signal quality score s as shown in FIG. 14 and feeds back the signal quality as a weight for calculating the reliability of the representative value of the prediction label. A calculation method for the reliability r of the representative value in a case where the signal quality is fed back can be defined as shown in the following expression (3) based on Expression (1) above.

[Expression 3]

$$r(t) = \sum_i w_i c_i s_i y_i \Delta t_i / \sum_i w_i \Delta t_i \qquad (3)$$

It should be noted that $s_i$ denotes a signal quality score [0.0 1.0] of the i-th event.

In accordance with Expression (3) above, with respect to the reliability of the prediction label of the emotion status in the plurality of events detected in the sliding window, reliability of the representative value of the prediction label in the sliding window is calculated as consecutive values of [−1 1].

In addition, as in the first embodiment, a representative value z of the prediction label is calculated as an emotion estimation result by threshold-processing an output r of Expression (3) and substituting it into Expression (2) above.

It should be noted that the following expression (4) may replace Expression (3) above.

[Expression 4]

$$r(t) = \sum_i w_i c_i s_i y_i \Delta t_i / \sum_i w_i s_i \Delta t_i \qquad (4)$$

Expression (3) has a property that the reliability r is lower in the sliding window with lower signal quality. With respect to Expression (3) having such a property, Expression (4) can be normalized by including $s_i$ as the denominator. Accordingly, uniform emotion determination can be performed between the sliding windows with different signal quality. Expression (4) can replace Expression (3) thereafter.

Generally-Used Signal Quality Determination Processing

Lawhern, Vernon, W. David Hairston, and Kay Robbins. "DETECT: A MATLAB toolbox for event detection and identification in time series, with applications to artifact detection in the EEG signals." PloS one 8.4 (2013): e62944. (hereinafter, referred to as Cited Document 4) has described a generally-used technology based on which the signal quality determination unit 201 determines the signal quality.

Figure 15:
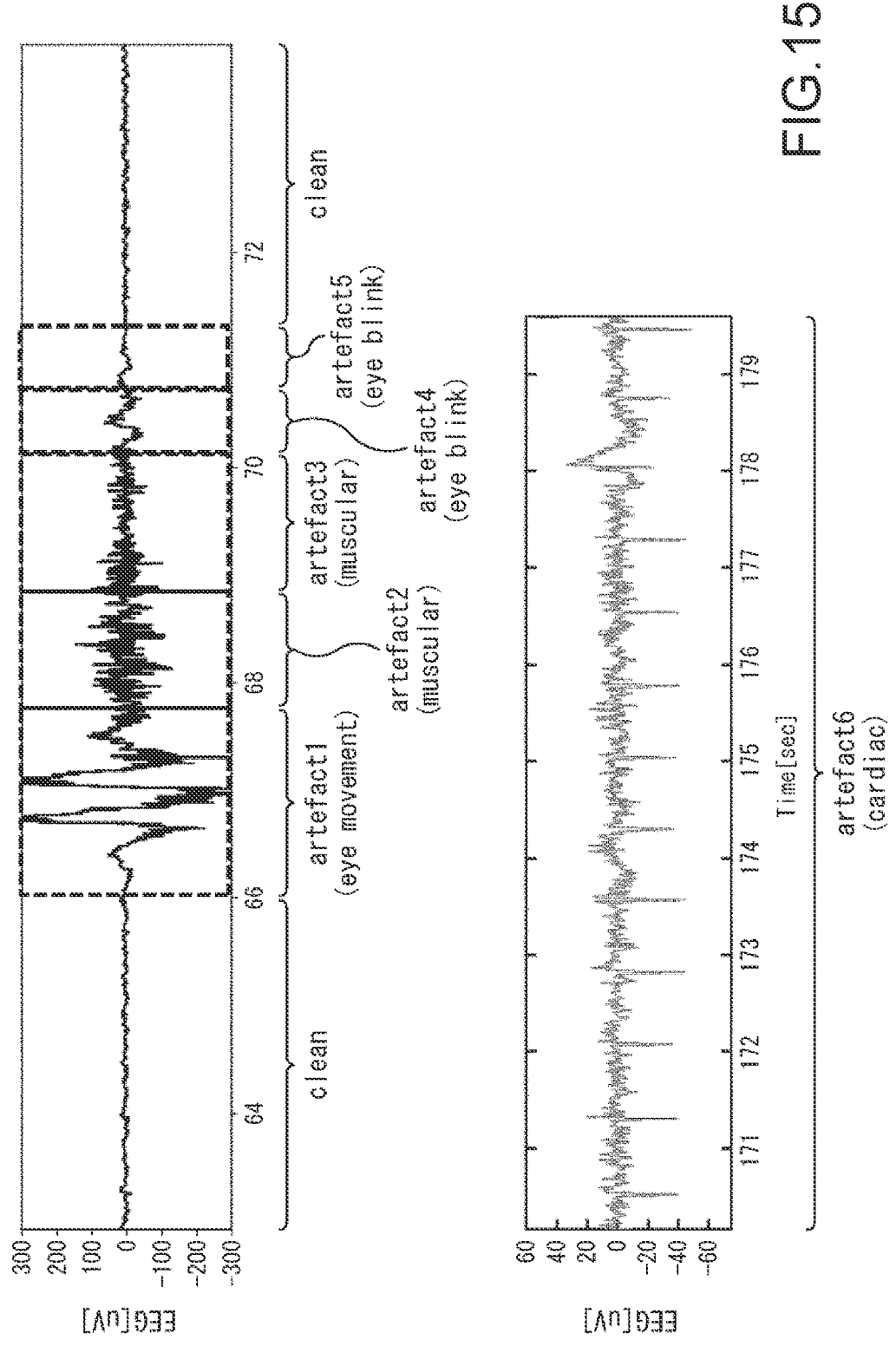
FIG. 15 A diagram showing an example of a waveform of an electroencephalographic signal for each time.

In the technology according to Cited Document 4, as shown in FIG. 15, an electroencephalographic signal configured with a plurality of channels is input and the waveform is analyzed.

FIG. 15 is a diagram showing an example of the waveform of the electroencephalographic signal for each time.

In a case of measuring the electroencephalogram in an actual environment, various types of noise are superimposed on the electroencephalographic signal as shown in FIG. 15 because of the user's movement.

No noise is superimposed on the electroencephalographic signal for the time of t=63 to t=66 and the time of t=71 to t=74. It should be noted that the signals with no noise superimposed thereon are shown as "Clean" in the figure.

Artifact 1=an eyeball movement noise (in the figure, "Eye-movement") is superimposed on the electroencephalographic signal for the time of t=66 to t=68. The eyeball movement noise is noise generated on the electroencephalographic signal especially on the forehead, for example, when the human moves the line of sight.

Artifacts 2 and 3=electromyography noise (in the figure, "Muscular") is superimposed on the electroencephalographic signal for the time of t=68 to t=70. The electromyography noise is noise generated in the electroencephalographic signal, for example, when the human makes a facial expression or moves his or her muscles during a conversation.

Artifacts 4 and 5=eyeblink noise (in the figure, "Eyeblink") are superimposed on the electroencephalographic signal for the time of t=70 to t=72. The eyeblink noise is noise generated in the electroencephalographic signal especially on the forehead, for example, when the frequency and strength of the human blink change.

Artifact 6=electrocardiogram noise (in the figure, "Cardiac") is superimposed on the electroencephalographic signal for the time of t=170 to t=180. A change derived from the human heart rate can appear as a potential change and the potential displacement can be the electrocardiogram noise on the electroencephalographic signal.

As described above, the electroencephalographic signals with the various types of noise superimposed thereon have different waveforms. Therefore, a signal waveform in the generation area of each artifact is discriminated by analyzing the waveform, and an artifact type is discriminated. At that time, pattern matching, signal processing for waveform discrimination, and machine learning technologies for example are used for determining the signal quality.

For example, Khatwani, Mohit, et al. "Energy efficient convolutional neural networks for eeg artifact detection." 2018 IEEE Biomedical Circuits and Systems Conference (BioCAS). IEEE, 2018. (hereinafter, referred to as Cited Document 5) has described the machine learning technology used for determining the signal quality.

In the technology according to Cited Document 5, discrimination based on a discriminative model that is a machine learning model is performed, such that the class is discriminated for each waveform of the biological signal. Based on the class discrimination result, the signal quality is determined.

The signal quality determination unit 201 further calculates a signal quality score (SQE score) specialized for the processing (Expression (3)) in the stabilization processing unit 202 by using the above-mentioned signal quality determination technology as the basis.

Signal Quality Determination Using Electroencephalogram

FIG. 16 is a diagram showing an example of quality stability determination using an electroencephalogram.

In case of measuring the electroencephalogram in an actual environment, a signal (in the figure, "observed EEG Signal") with various types of noise (in the figure, e.g., "Eye-movement", "Muscular", "Eyeblink", "Cardiac") superimposed on the electroencephalographic signal (in the figure, "EEG") because of the user's movement as described above with reference to FIG. 15 is detected.

These types of noise are naturally generated when the user experiences an application in an ordinary environment or actual environment, and these often cannot be completely cancelled by filtering because of factors such as the user's situation and limitations on the apparatus.

In view of this, in the second embodiment, a discriminative class in a case where each noise is generated is defined in advance, and a discriminative model based on supervised learning is built. Hereinafter, the discriminative model for quality determination will be referred to as an SQE discriminative model using the capitals of Signal Quality Estimation, and the discriminative class defined in advance will be referred to as an SQE discriminative class.

The signal quality determination unit 201 discriminates a waveform type on the basis of the SQE discriminative model. Then, the signal quality determination unit 201 calculates a signal quality score s specialized for the signal processing method defined in Expression (3). The signal quality score s is calculated in accordance with the following expression (5).

[Expression 5]

$$s_m = \alpha_m f(d_m) \qquad (5)$$

Where m denotes the SQE discriminative class, $\alpha_m$ denotes the class label (constant: previous setting [0, 1])

corresponding to the SQE discriminative class, $d_m$ denotes the reliability of the class label obtained from the SQE discriminative model (that depends on the input signal [0, 1]), and f( ) denotes a function and is defined as a look-up table for adjustment (previous setting [0, 1]).

"$\alpha$" is an adjustment term considering a noise cancellation performance difference of the filter pre-processing unit 101 in accordance with a noise type discriminated on the basis of the SQE discriminative class.

In the present technology, in a case where it is discriminated that the electroencephalographic signal is clean on the basis of the SQE discriminative model, a look-up table in which f( ) monotonically increases is set so that the weight is increased as the reliability of the class label obtained from the SQE discriminative model increases in Expression (3), such that it is discriminated to be a positive class.

Here, the positive class refers to a class whose signal quality is discriminated to be good on the basis of a predetermined threshold. The negative class refers to a class whose signal quality is discriminated to be bad and contain noise on the basis of the predetermined threshold.

In a case where the electroencephalographic signal is clean, the weight is set as $\alpha=1.0$ at maximum. In a case where noise has been generated in the electroencephalographic signal, a look-up table in which f( ) monotonically decreases is set so that the weight is decreased as the reliability of the class label obtained from the SQE discriminative model increases in Expression (3), such that it is discriminated to be a positive class.

"$\alpha$" is adjusted in accordance with the SQE discriminative class and the performance difference of the filter pre-processing unit 101. For example, "$\alpha$" is set to be relatively larger, $\alpha_m=0.9$, for example with respect to the eyeblink noise that can be relatively easily cancelled by signal processing. "$\alpha$" is set to be relatively smaller, $\alpha_m=0.2$, for example with respect to the electromyography noise that is principally difficult to be cancelled by signal processing in the filter pre-processing unit 101.

It should be noted that in the present technology, $\alpha_m$ is an adjustment term and the value is not limited.

"$f(d_m)$" monotonically increases in a case where m is a main signal and monotonically decreases in a case where m is noise.

As described above, defining Expression (5) above allows the signal quality score s [0.0 1.0] to increase in value as the signal quality increases and to decrease in value as the signal quality decreases. It is established as the signal processing method specialized for Expression (3).

Moreover, the example in which the SQE discriminative model determines the signal quality at each time from all channels has been described. However, in the present technology, the signal quality of the SQE discriminative model may be determined on a channel-by-channel basis.

In addition, a case where processing of estimating an emotion on the basis of a plurality of types of biological signal modals (e.g., multimodal signals such as an electroencephalogram (EEG), the pulse waves (PPG), and sweating (EDA)) is also set as a target, an SQE discriminative model is built for each of the biological signal modals, and signal quality is determined is conceived in the present technology.

Therefore, a modified example further extended for coping with such a case with respect to Expression (5) above will be described.

Weight of Signal Quality Score

FIG. 17 is a diagram showing an example of calculating the weight of the signal quality score (SQE score) per each type and each channel.

The right side of FIG. 17 shows a graph showing a degree of contribution to discrimination of the emotion status in a feature amount corresponding to a signal of each type and each channel.

The graph shows feature amounts ($\theta$ waves, $\alpha$ waves, and $\beta$ waves) calculated on the basis of an electroencephalogram, feature amounts (average heart rate, RMSSD, and LF/HF) calculated on the basis of pulse waves, and feature amounts (SCL and SCR) calculated on the basis of sweating.

The graph shows an example in which the machine learning model is an emotion estimation model constituted by three (j=3) types of biological signals.

At this time, as shown on the right side of FIG. 17, it is necessary to calculate j-types of the biological signal by using an integrated signal quality score s as a scalar value in order to apply it to Expression (3) above.

In the present technology, performing weighted summation of the SQE score for each of the j-types of signals determines the integrated signal quality score s as an estimation result. Specifically, the signal quality score s is calculated in accordance with the following expression (6).

[Expression 6]

$$s_m = \sum_j W_j \alpha_{m,j} f(d_{m,j}) / \sum_j W_j \qquad (6)$$

It should be noted that the degree-of-model contribution sum $W_j$ is expressed as the following expression (7).

[Expression 7]

$$W_j = \sum_{k \in F_j} |w_{jk}| \qquad (7)$$

That is, the scalar value of the integrated signal quality score at each time is calculated by calculating a degree-of-model contribution sum of the feature amount belonging to the signal j as $W_j$ once and adding $W_j$ as the weight of the signal quality score of the signal j.

As described above, the present technology can be applied also in a case of calculating an SQE score weight per each type and each channel.

Processing of Apparatus

Figure 18:
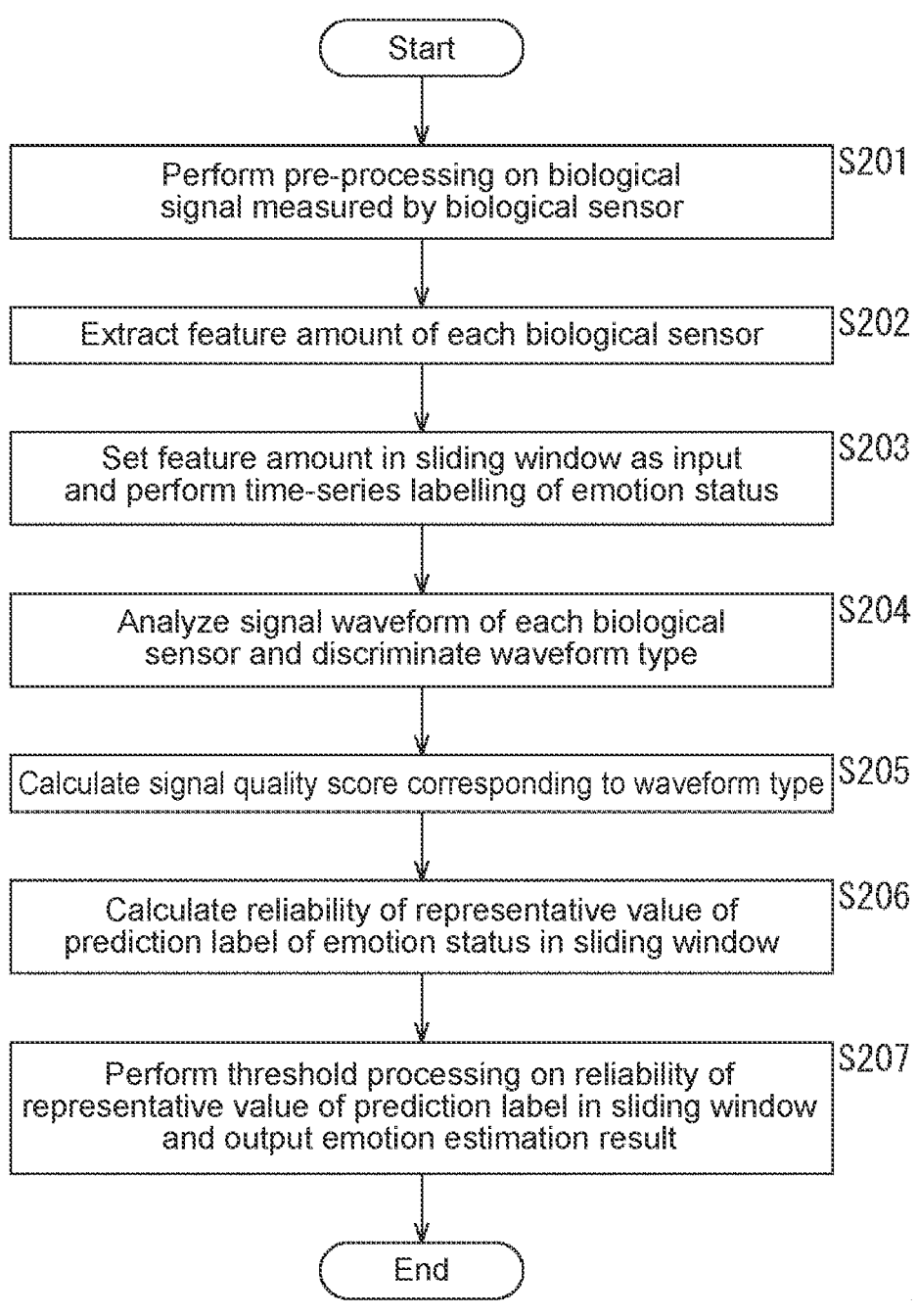
FIG. 18 A flowchart describing processing of the biological information processing apparatus in FIG. 12.

FIG. 18 is a flowchart describing processing of the biological information processing apparatus 11 in FIG. 12.

Processing similar to that of Steps S101 to S103 in FIG. 11 are performed as Steps S201 to S203 in FIG. 18, and therefore descriptions thereof will be omitted.

In FIG. 18, the processing of Steps S204 and S205 is performed in parallel to the processing of Step S201 to S203.

In Step S204, the signal quality determination unit 201 analyzes a signal waveform of each biological sensor and discriminates a waveform type.

In Step S205, the signal quality determination unit 201 calculates a signal quality score corresponding to the waveform type. The signal quality determination unit 201 outputs the calculated signal quality score to the stabilization processing unit 202.

In Step S206, the stabilization processing unit 202 sets the labels of the emotion status in a time-series supplied from the emotion status time-series labelling unit 103 and the signal quality score supplied from the stabilization processing unit 202, as an input, and calculates reliability r of the representative value of the prediction label in the sliding window in accordance with Expression (3) above.

In Step S207, the stabilization processing unit 202 performs threshold processing on the reliability r of the representative value of the prediction label in accordance with Expression (2) above and outputs the representative value z of the prediction label as the emotion estimation result.

As described above, in the second embodiment of the present technology, the emotion estimation result is output on the basis of a result of performing weighted summation of the signal quality determination result with the reliability of the prediction label. Therefore, the robustness of the estimation accuracy of the emotion estimation is further improved as compared to the first embodiment.

It should be noted that although the example in which the signal quality is determined by the machine learning approach has been described above, the signal quality may be determined by an approach other than the machine learning.

For example, a heart rate sensor (photoplethysmography (PPG)) may be employed. The pulse waves have strong periodicity corresponding to pulsation when they can be normally measured. The signal periodicity lowers when noise such as body movement noise is generated.

In view of this, WO 2017/199597 (hereinafter, referred to as Cited Document 6) has described that the periodicity of a pulse wave signal is assessed by analyzing an autocorrelation of the signal (relationship between the amount of shift of the signal itself and the correlation value). With the technology according to Cited Document 6, for example, the periodicity is recognized to be low when the autocorrelation value is low, and the signal quality can be determined.

Therefore, the signal quality determination unit 201 may output the signal quality score corresponding to high/low of the signal periodicity without machine learning.

It should be noted that this technology is not limited to the pulse waves, and can be applied to biological signals with high periodicity such as blood flow and a continuous blood pressure.

5. Others

Effects of Present Technology

In recent years, wearable devices which can be used in a daily life environment, such as a wristband, a headband, and earphones, measure nervous activities contributing to changes in emotion with less load on users. In particular, it is desirable to easily measure autonomous nervous activities (e.g., pulse waves and sweating).

It is also desirable to achieve emotion estimation by sensing an electroencephalogram through a wearable device that can be naturally mounted on the head, e.g., a virtual reality (VR) head-mounted display or a wearable device naturally adaptable for the user's experience, e.g., an earphones- or headphones-type wearable device according to a technology for measuring an electroencephalogram inside/around an ear such as In-ear EEG/Around-ear EEG, which have been actively studied in recent years.

On the other hand, there is an influence of a user's body movement in applications in daily life and an actual environment. Since the biological signal typically has low signal intensity, it is necessary to improve the robustness against the noise influence due to the user's body movement in order to perform accurate sensing in daily life and an actual environment.

In view of this, in the present technology, an emotion estimation result is output on the basis of a result of performing weighted summation of a prediction label with prediction label reliability that is reliability of the prediction label.

It leads to an improvement in the robustness of the emotion estimation against noise and an improvement in the accuracy of the emotion estimation.

In addition, in the present technology, the emotion estimation result is output on the basis of a result of performing weighted summation of the reliability of the prediction label of the emotion status and the signal quality determination result.

Therefore, extension of an actual application involving the user's body movement can be expected.

Development to a variety of applications involving body movements, for example, monitoring of a stress status in daily life, visualization of a concentrated status in an office environment, engagement analysis of a user while the user is watching video content, or excitement analysis during game play can be expected.

excitement analysis during game play can be expected.

Configuration Example of Computer

The above-mentioned series of processing may be executed by hardware or may be executed by software. If the series of processing is executed by software, programs that configure the software are installed, from the program recording medium, in a computer incorporated in dedicated hardware or a general-purpose personal computer for example.

Figure 19:
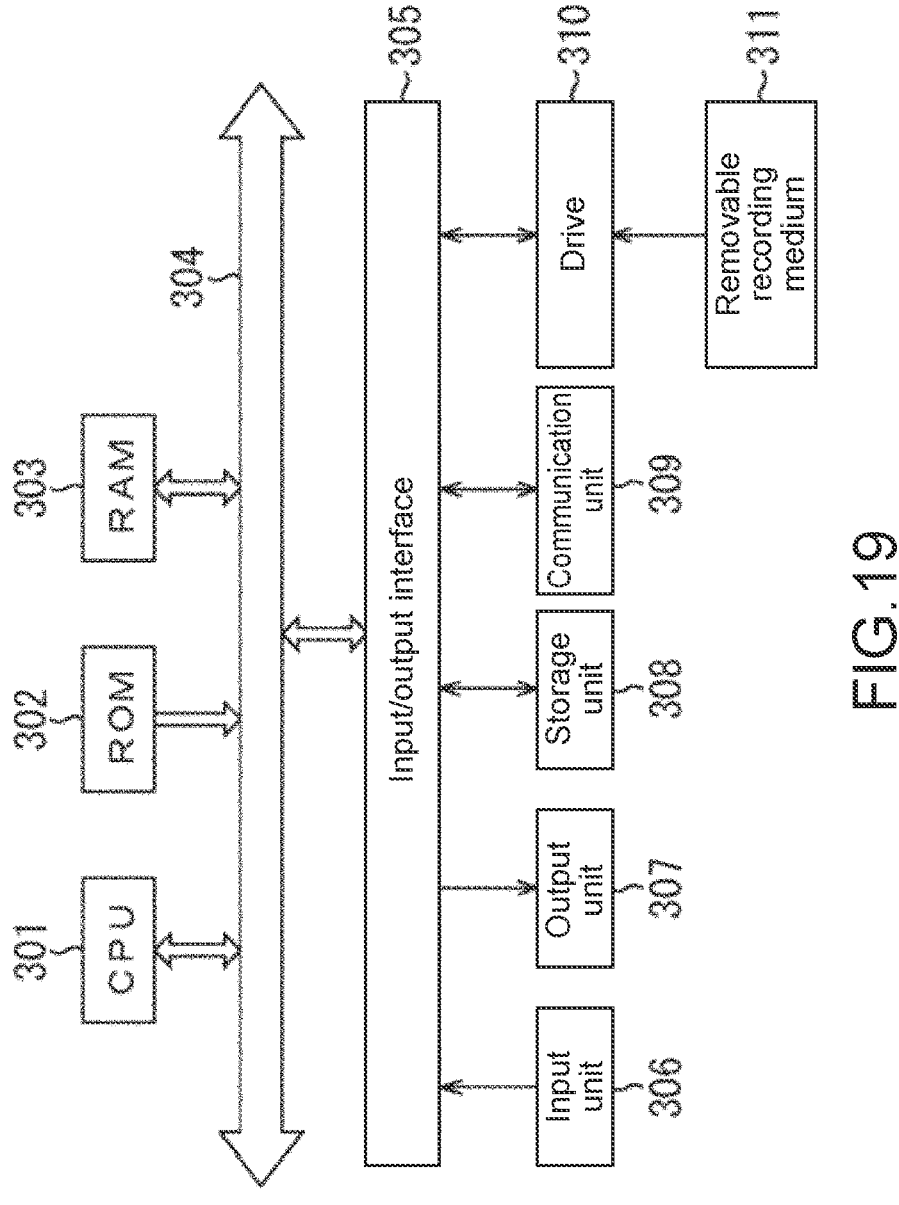
FIG. 19 A block diagram showing a configuration example of a computer.

FIG. 19 is a block diagram showing a configuration example of hardware of the computer that executes the above-mentioned series of processing in accordance with the program.

A central processing unit (CPU) 301, a read only memory (ROM) 302, and a random access memory (RAM) 303 are connected to one another through a bus 304.

An input/output interface 305 is also connected to the bus 304. An input unit 306 constituted by a keyboard, a mouse, and the like and an output unit 307 constituted by a display, a loudspeaker, and the like are connected to the input/output interface 305. Moreover, a storage unit 308 constituted by a hard disk, a nonvolatile memory, and the like, a communication unit 309 constituted by a network interface and the like, and a drive 310 that drives a removable medium 311 are connected to the input/output interface 305.

In the thus configured computer, the CPU 301 loads, for example, programs stored in the storage unit 308 into the RAM 303 via the input/output interface 305 and the bus 304 and executes them. In this manner, the above-mentioned series of processing is performed.

Programs executed by the CPU 301 can be, for example, provided recorded on the removable medium 311 that is a package medium or provided via a wired or wireless transmission medium such as a local area network, the Internet, and digital broadcasting and installed in the storage unit 308.

It should be noted that the programs executed by the computer may be programs processed chronologically in the order described in the present specification or may be programs processed concurrently or at a required time, e.g., upon calling.

It should be noted that in the present specification, the system means a set of a plurality of components (apparatuses, modules (parts), etc.) and it does not matter whether or not all the components are contained in the same casing.

Therefore, a plurality of apparatuses housed in separate casings and connected via a network and a single apparatus including a plurality of modules housed in the same casing are both considered as the system.

Moreover, the effects set forth herein are merely exemplary and not limitative, and other effects may be provided.

Embodiments of the present technology are not limited to the above-mentioned embodiments and various modifications can be made without departing from the gist of the present technology.

For example, the present technology can take a cloud computing configuration in which a plurality of apparatuses shares and cooperatively processes a single function via a network.

Moreover, a plurality of apparatuses can share and execute the respective steps described above with reference to the above-mentioned flowcharts rather than executing them by a single apparatus.

In addition, if a single step is constituted by a plurality of processes, a plurality of apparatuses can share and execute the plurality of processes of the single step rather than executing them by a single apparatus.

Combination Examples of Configurations

The present technology can also take the following configuration.

(1) A signal processing apparatus, including:

a feature amount extraction unit that extracts, on the basis of a measured biological signal, a physiological measure contributing to an emotion as a feature amount;

an emotion status time-series labelling unit that outputs, with respect to time-series data about the feature amount, time-series data about a prediction label of an emotion status by a discriminative model built in advance; and a stabilization processing unit that outputs an emotion estimation result on the basis of a result of performing weighted summation of the prediction label with prediction label reliability that is reliability of the prediction label.

(2) The signal processing apparatus according to (1), in which the emotion status time-series labelling unit outputs, with respect to the time-series data about the feature amount in a sliding window, the time-series data about the prediction label of the emotion status in the sliding window by the discriminative model.

(3) The signal processing apparatus according to claim (1) or (2), in which the stabilization processing unit calculates measure-of-central-tendency reliability that is reliability of a representative value of the prediction label by performing weighted summation of the prediction label and the prediction label reliability and outputs the representative value of the prediction label as the emotion estimation result by threshold processing on the measure-of-central-tendency reliability.

(4) The signal processing apparatus according to (3), in which the stabilization processing unit calculates the measure-of-central-tendency reliability in accordance with the following expression

[Expression 1]

$$r(t) = \sum_i w_i c_i y_i \Delta t_i / \sum_i w_i \Delta t_i$$

where y denotes the prediction label, c denotes the prediction label reliability, and $\Delta t_i$ denotes a continuation time of an i-th segment.

(5) The signal processing apparatus according to (1) or (2), further including a signal quality determination unit that determines signal quality of the biological signal, in which the stabilization processing unit outputs the emotion estimation result on the basis of a result of performing weighted summation of the prediction label with the prediction label reliability and a determination result of the signal quality.

(6) The signal processing apparatus according to (5), in which the stabilization processing unit calculates measure-of-central-tendency reliability that is reliability of a representative value of the prediction label by performing weighted summation of the prediction label with the prediction label reliability and the determination result of the signal quality and outputs the representative value of the prediction label as the emotion estimation result by threshold processing on the measure-of-central-tendency reliability.

(7) The signal processing apparatus according to (6), in which the stabilization processing unit calculates the measure-of-central-tendency reliability in accordance with the following expression

[Expression 3]

$$r(t) = \sum_i w_i c_i s_i y_i \Delta t_i / \sum_i w_i \Delta t_i$$

where y denotes the prediction label, c denotes the prediction label reliability, s denotes a signal quality score that is the determination result of the signal quality, and $\Delta t_i$ denotes a continuation time of an i-th event.

(8) The signal processing apparatus according to (7), in which the signal quality determination unit outputs the signal quality score for each class m in accordance with the following expression by using two or more types of class labels a discriminated by a discriminative model for quality determination, reliability d of each of the class labels, and a function f( ) for adjusting the reliability d

[Expression 5]

$$s_m = \alpha_m f(d_m).$$

(9) The signal processing apparatus according to (8), in which as to one or more types of respective classes, the function f( ) monotonically increases with respect to a class having the signal quality discriminated to be better than a predetermined threshold and monotonically decreases with respect to a class having the signal quality discriminated to be worse than the predetermined threshold and contain noise.

(10) The signal processing apparatus according to (7), in which the signal quality determination unit outputs the signal quality score depending on high/low of signal periodicity.

(11) The signal processing apparatus according to (7), in which the stabilization processing unit calculates, in a case where the feature amount extracted from j-types of the biological signals is set to be an input variable, the measure-of-central-tendency reliability of the prediction label in the sliding window in accordance with the following expression

[Expression 3]

$$r(t) = \sum_i w_i c_i s_i y_i \Delta t_i / \sum_i w_i \Delta t_i$$

on the basis of a result of performing weighted summation of the signal quality score for each of the j-types of the biological signals.

(12) The signal processing apparatus according to (11), in which assuming that $w_{jk}$ denotes a degree of model contribution of a feature amount k belonging to j-types of signals, a weight $W_j$ in weighted-sum calculation of the signal quality score is expressed in accordance with the following expression

[Expression 7]

$$W_j = \sum_{k \in F_j} |w_{jk}|,$$

and
is calculated in accordance with the following expression

[Expression 6]

$$s_m = \sum_j W_j \alpha_{m,j} f(d_{m,j}) / \sum_j W_j.$$

(13) The signal processing apparatus according to (6), in which the stabilization processing unit calculates the measure-of-central-tendency reliability in accordance with the following expression

[Expression 4]

$$r(t) = \sum_i w_i c_i s_i y_i \Delta t_i / \sum_i w_i s_i \Delta t_i$$

(where y denotes the prediction label, c denotes the reliability of the prediction label, s denotes a signal quality score, and $\Delta t_i$ denotes a continuation time of an i-th event).

(14) The signal processing apparatus according to any of (1) to (13), in which the biological signal is a signal obtained by measuring at least one of an electroencephalogram, emotional sweating, a pulse wave, blood flow, or a continuous blood pressure.

(15) The signal processing apparatus according to any of (1) to (14), further including a biological sensor that measures the biological signal.

(16) The signal processing apparatus according to any of (1) to (15), in which a casing is configured to be wearable.

(17) A signal processing method, including:

by a signal processing apparatus, extracting, on the basis of a measured biological signal, a physiological measure contributing to an emotion as a feature amount;

outputting, with respect to time-series data about the feature amount, time-series data about a prediction label of an emotion status by a discriminative model built in advance; and outputting an emotion estimation result on the basis of a result of performing weighted summation of the prediction label with prediction label reliability that is reliability of the prediction label.

REFERENCE SIGNS LIST 1 emotion estimation processing system
11 biological information processing apparatus
12 server
13 terminal apparatus
14 network
101 filter pre-processing unit
102 feature amount extraction unit
103 emotion status time-series labelling unit
104 stabilization processing unit
201 signal quality determination unit
202 stabilization processing unit

What is claimed is:

1. A signal processing apparatus, comprising:

a biological sensor that measures a biological signal of a living body;

a second sensor that measures a body movement signal representative of changes in body movement of the living body;

a feature amount extraction unit operably coupled to the biological sensor and the second sensor, and that extracts, on a basis of the biological signal measured by the biological sensor, a physiological measure contributing to an emotion as a feature amount, wherein to reduce body movement noise in the biological signal measured by the biological sensor, the feature amount extraction unit extracts the physiological measure further on a basis of the body movement signal measured by the second sensor;

an emotion status time-series labelling unit that outputs, with respect to time-series data about the feature amount, time-series data about a prediction label of an emotion status by a discriminative model built in advance;

a signal quality determination unit that determines a signal quality of the biological signal; and a stabilization processing unit that outputs an emotion estimation result on a basis of a result of performing a weighted summation of the prediction label with a prediction label reliability and a determination result of the signal quality, wherein the prediction label reliability is a reliability of the prediction label, wherein the stabilization processing unit calculates a measure-of-central-tendency reliability that is a reliability of a representative value of the prediction label by performing a weighted summation of the prediction label with the prediction label reliability and the determination result of the signal quality and outputs the representative value of the prediction label as the emotion estimation result by threshold processing on the measure-of-central-tendency reliability, and wherein the stabilization processing unit calculates the measure-of-central-tendency reliability in accordance with the expression $$r(t) = \sum_i w_i c_i s_i y_i \Delta t_i \Big/ \sum_i w_i \Delta t_i$$

where y denotes the prediction label, c denotes the prediction label reliability, s denotes a signal quality score that is the determination result of the signal quality, and $\Delta t_i$ denotes a continuation time of an i-th event.

2. The signal processing apparatus according to claim 1, wherein the emotion status time-series labelling unit outputs, with respect to the time-series data about the feature amount in a sliding window, the time-series data about the prediction label of the emotion status in the sliding window by the discriminative model.

3. The signal processing apparatus according to claim 1, wherein the signal quality determination unit outputs the signal quality score for each class m in accordance with the following expression by using two or more types of class labels discriminated by a discriminative model for quality determination, reliability d of each of the class labels, and a function f( ) for adjusting the reliability d $$s_m = \alpha_m f(d_m).$$

4. The signal processing apparatus according to claim 3, wherein as to one or more types of respective classes, the function f( ) monotonically increases with respect to a class having the signal quality discriminated to be better than a predetermined threshold and monotonically decreases with respect to a class having the signal quality discriminated to be worse than the predetermined threshold and contain noise.

5. The signal processing apparatus according to claim 1, wherein the signal quality determination unit outputs the signal quality score depending on a high/low of signal periodicity.

6. The signal processing apparatus according to claim 1, wherein the stabilization processing unit calculates, in a case where the feature amount extracted from j-types of biological signals is set to be an input variable, the measure-of-central-tendency reliability of the prediction label in a sliding window in accordance with the expression and on a basis of a result of performing a weighted summation of the signal quality score for each of the j-types of the biological signals.

7. The signal processing apparatus according to claim 6, wherein assuming that $w_{jk}$ denotes a degree of model contribution of a feature amount k belonging to the j-types of biological signals, a weight Wj in a weighted-sum calculation of the signal quality score is expressed in accordance with the following expression $$W_j = \sum_{k \in F_j} |w_{jk}|,$$

and
is calculated in accordance with the following expression $$s_m = \sum_j W_j \alpha_{m,j} f(d_{m,j}) / \sum_j W_j.$$

8. The signal processing apparatus according to claim 1, wherein the biological signal is a signal obtained by measuring at least one of an electroencephalogram, emotional sweating, a pulse wave, blood flow, or a continuous blood pressure.

9. The signal processing apparatus according to claim 1, further comprising a third sensor operably coupled to the feature amount extraction unit and that measures a pressure signal representative of changes in pressure of the living body in a detection area of the biological sensor, wherein to reduce body movement noise in the biological signal measured by the biological sensor, the feature amount extraction unit extracts the physiological measure further on a basis of the pressure signal measured by the third sensor.

10. The signal processing apparatus according to claim 1, wherein a casing is configured to be wearable.

11. A signal processing method, comprising:
by a signal processing apparatus,
extracting, on a basis of a biological signal of a living body measured by a biological sensor, a physiological measure contributing to an emotion as a feature amount, wherein the extracting comprises reducing body movement noise in the biological signal by extracting the physiological measure further on a basis of a body movement signal of the living body measured by a second sensor;
outputting, with respect to time-series data about the feature amount, time-series data about a prediction label of an emotion status by a discriminative model built in advance;
determining a signal quality of the biological signal; and
outputting an emotion estimation result on a basis of a result of performing a weighted summation of the prediction label with a prediction label reliability and a determination result of the signal quality, wherein the prediction label reliability is a reliability of the prediction label, and wherein outputting the emotion estimation result comprises:
calculating a measure-of-central-tendency reliability that is a reliability of a representative value of the prediction label by performing a weighted summation of the prediction label with the prediction label reliability and the determination result of the signal quality and outputting the representative value of the prediction label as the emotion estimation result by threshold processing on the measure-of-central-tendency reliability, wherein the calculating comprises calculating the measure-of-central-tendency reliability in accordance with the expression $$r(t) = \sum_i w_i c_i s_i y_i \Delta t_i / \sum_i w_i \Delta t_i$$

where y denotes the prediction label, c denotes the prediction label reliability, s denotes a signal quality score that is the determination result of the signal quality, and $\Delta t_i$ denotes a continuation time of an i-th event.

12. The signal processing method according to claim 11, wherein the reducing comprises reducing the body movement noise in the biological signal by extracting the physiological measure further on a basis of a pressure signal representative of changes in pressure of the living body in a detection area of the biological sensor measured by a third sensor.

13. The signal processing method according to claim 11, wherein, in a case where the feature amount extracted from j-types of biological signals is set to be an input variable, the calculating comprises calculating the measure-of-central-tendency reliability of the prediction label in a sliding window in accordance with the expression
and on a basis of a result of performing weighted summation of the signal quality score for each of the j-types of the biological signals, and wherein the method further comprises calculating a weight Wj in a weighted-sum calculation of the signal quality score in accordance with the following expression $$s_m = \sum_j W_j \alpha_{m,j} f(d_{m,j}) / \sum_j W_j,$$

wherein Wj is expressed in accordance with the following expression $$W_j = \sum_{k \in F_j} |w_{jk}|,$$

and wherein $w_{jk}$ denotes a degree of model contribution of a feature amount k belonging to the j-types of biological signals.

14. The signal processing method according to claim 11, further comprising outputting, with respect to the time-series data about the feature amount in a sliding window, the time-series data about the prediction label of the emotion status in the sliding window by the discriminative model.

15. The signal processing method according to claim 11, further comprising outputting the signal quality score depending on a high/low of signal periodicity.

* * * * *